(12) United States Patent
Melodia et al.

(10) Patent No.: US 11,813,037 B2
(45) Date of Patent: Nov. 14, 2023

(54) TRANSMISSION AND MEDIUM ACCESS CONTROL TECHNIQUES FOR ULTRASONIC COMMUNICATIONS IN THE BODY

(71) Applicant: The Research Foundation for The State University of New York, Amherst, NY (US)

(72) Inventors: Tommaso Melodia, Newton, MA (US); Giuseppe Enrico Santagati, Cambridge, MA (US); Laura Galluccio, Trecastagni (IT); Sergio Palazzo, San Giovanni la Punta (IT)

(73) Assignee: The Research Foundation for The State University of New York, Amherst, NY (US)

( * ) Notice: Subject to any disclaimer, the term of this patent is extended or adjusted under 35 U.S.C. 154(b) by 139 days.

(21) Appl. No.: 17/157,251

(22) Filed: Jan. 25, 2021

(65) Prior Publication Data
US 2021/0353147 A1  Nov. 18, 2021

Related U.S. Application Data

(63) Continuation of application No. 15/025,622, filed as application No. PCT/US2014/058492 on Sep. 30, 2014, now Pat. No. 10,898,076.
(Continued)

(51) Int. Cl.
*A61B 5/00* (2006.01)
*G08C 23/02* (2006.01)
(Continued)

(52) U.S. Cl.
CPC .......... *A61B 5/0028* (2013.01); *A61B 5/0015* (2013.01); *A61B 5/0024* (2013.01);
(Continued)

(58) Field of Classification Search
CPC ....... A61B 5/00; A61B 5/0015; A61B 5/0024; A61B 5/0028; A61B 5/0031; A61B 5/021;
(Continued)

(56) References Cited

U.S. PATENT DOCUMENTS

| 4,045,767 A | 8/1977 | Nishihara et al. |
| 6,056,695 A | 5/2000 | Rupp et al. |

(Continued)

FOREIGN PATENT DOCUMENTS

WO   2013/168170 A1   11/2013

OTHER PUBLICATIONS

R. Di, S. Peng, S. Taylor and Y. Morton, "A USRP-based GNSS and interference signal generator and playback system," Proceedings of the 2012 IEEE/ION Position, Location and Navigation Symposium, 2012, pp. 470-478, doi: 10.1109/PLANS.2012.6236916. (Year: 2012).*

(Continued)

*Primary Examiner* — Daniel L Murphy
*Assistant Examiner* — Amie M Ndure
(74) *Attorney, Agent, or Firm* — Hodgson Russ LLP

(57) ABSTRACT

Methods and devices for transmitting and receiving data through biological tissue using ultrasonic pulses are described. Methods of the present invention may set an initial time-hopping frame length and an initial spreading code length for data transmission. A request-to-transmit may be sent from a transmitter over a control channel at the initial frame and code length. The receiver may respond to the transmitter with a clear-to-transmit packet having feedback information. The feedback information can be used to improve a forward time-hopping frame length and a forward spreading code length. Embodiments of the invention may involve a body area network or body surface network (Continued)

comprising a plurality of implanted sensor nodes operating according to the disclosed invention.

8 Claims, 29 Drawing Sheets

Related U.S. Application Data

(60) Provisional application No. 61/884,320, filed on Sep. 30, 2013.

(51) Int. Cl.
*H04Q 9/00* (2006.01)
*H04B 1/7163* (2011.01)
*A61B 5/08* (2006.01)
*A61B 5/026* (2006.01)
*A61B 5/024* (2006.01)
*A61B 5/145* (2006.01)
*A61B 5/021* (2006.01)
*H04B 1/69* (2011.01)

(52) U.S. Cl.
CPC ......... *G08C 23/02* (2013.01); *H04B 1/71635* (2013.01); *H04Q 9/00* (2013.01); *A61B 5/0031* (2013.01); *A61B 5/021* (2013.01); *A61B 5/024* (2013.01); *A61B 5/026* (2013.01); *A61B 5/0816* (2013.01); *A61B 5/14532* (2013.01); *A61B 5/14542* (2013.01); *H04B 2001/6908* (2013.01)

(58) Field of Classification Search
CPC ....... A61B 5/024; A61B 5/026; A61B 5/0816; A61B 5/14532; A61B 5/14542; G08C 23/02; H04B 1/7163; H04B 1/71635; H04B 2001/6908; H04Q 9/00
See application file for complete search history.

(56) References Cited

U.S. PATENT DOCUMENTS

| | | |
|---|---|---|
| 6,148,342 A | 11/2000 | Ho |
| 7,945,064 B2 | 5/2011 | O'Brien, Jr. et al. |
| 8,422,337 B2 | 4/2013 | Su et al. |
| 8,512,241 B2 | 8/2013 | Bandy et al. |
| 8,626,296 B2 | 1/2014 | Von Arx et al. |
| 2002/0018514 A1 | 2/2002 | Haynes et al. |
| 2002/0050983 A1 | 5/2002 | Liu et al. |
| 2002/0110203 A1 | 8/2002 | Sarkar |
| 2002/0143245 A1 | 10/2002 | Rather et al. |
| 2002/0196845 A1 | 12/2002 | Richards et al. |
| 2003/0095609 A1 | 5/2003 | Cowie et al. |
| 2003/0147480 A1 | 8/2003 | Richards et al. |
| 2004/0160916 A1 | 8/2004 | Vukovic et al. |
| 2004/0203697 A1 | 10/2004 | Finn |
| 2005/0089083 A1 | 4/2005 | Fisher et al. |
| 2005/0254553 A1 | 11/2005 | Yao et al. |
| 2007/0153873 A1 | 7/2007 | Fullerton et al. |
| 2007/0211786 A1 | 9/2007 | Shattil |
| 2008/0161660 A1 | 7/2008 | Ameson et al. |
| 2010/0098245 A1 | 4/2010 | Fang et al. |
| 2010/0298669 A1 | 11/2010 | Ida |
| 2012/0122392 A1 | 5/2012 | Morioka et al. |
| 2012/0130246 A1 | 5/2012 | Haider et al. |
| 2013/0197320 A1 | 8/2013 | Albert et al. |
| 2014/0050321 A1 | 2/2014 | Albert et al. |

OTHER PUBLICATIONS

Ettus Research, a National Instruments Brand. "USRP N210 Software Defined Radio (SDR)." Ettus Research, https://www.ettus.com/all-products/un210-kit. Sep. 14, 2012 (Year: 2012).*

Santagati, G.E., et al., Distributed MAC and Rate Adaptation for Ultrasonically Networked Implantable Sensors, IEEE International Conference, Feb. 6, 2013, 9 pages, http://arxiv.org/pdf/1302.0897.pdf.

Galluccio, et al., Challenges and Implications of Using Ultrasonic Communications in Intra-body Area Networks, 2012, 2012 9th Annual Conference on Wireless On-Demand Network Systems and Services (WONS), pp. 182-189.

Santagati, et al., Opto-ultrasonic communications for wireless intra-body nanonetworks, Nano Communication Networks, Mar. 12, 2014, vol. 5, pp. 3-14.

* cited by examiner

TRANSMISSION AND MEDIUM ACCESS CONTROL TECHNIQUES FOR ULTRASONIC COMMUNICATIONS IN THE BODY

CROSS-REFERENCE TO RELATED APPLICATIONS

This application is a continuation of U.S. application Ser. No. 15/025,622 filed on Mar. 29, 2016, which is a national phase of International Patent Application No. PCT/US2014/058492 filed on Sep. 30, 2014, which claims priority to U.S. Provisional Application No. 61/884,320 filed on Sep. 30, 2013, the disclosures of each of which are incorporated herein by reference.

STATEMENT REGARDING FEDERALLY SPONSORED RESEARCH

This invention was made with government support under grant no. CNS1253309 awarded by the National Science Foundation. The government has certain rights in the invention.

FIELD OF THE INVENTION

The invention relates to transmission and medium access control techniques for ultrasonic communications in biological tissue. For example, the invention relates to systems and methods for transmitting and receiving data through biological tissue using ultrasonic pulses.

BACKGROUND OF THE INVENTION

The use of miniaturized biomedical devices implanted in the human body and wirelessly internetworked is promising a significant leap forward in medical treatment of many pervasive diseases.

Body area networks have received considerable attention in the last few years, driven by the fascinating promise of a future where carefully engineered miniaturized biomedical devices implanted, ingested or worn by humans are wirelessly internetworked to collect diagnostic information and to fine-tune medical treatments over extended periods of time. Potential applications include, for example, measuring the level of glucose in the blood of diabetic patients, reactively controlling the administration of insulin through under-skin actuators, monitoring the digestive tract through pill-sized ingestible cameras, or monitoring bone-growth for diabetes treatment. Furthermore, these technologies may enhance minimally-intrusive microsurgery, thus over-coming the limitations of currently available catheter technology.

Yet, most research to date has focused on communications along the body surface among devices using traditional electromagnetic radio-frequency (RF) carrier waves, while the underlying challenge of enabling networked intra-body miniaturized (at the micro or nano scale) sensors and actuators that communicate through body tissues is substantially unaddressed. The main obstacle to enabling this vision of networked implantable devices is posed by the physical nature of propagation in the human body, which is composed primarily (65%) of water, a medium through which RF electromagnetic waves notoriously hardly propagate, even at relatively low frequencies. Accordingly, most research has focused on reducing the radiated power to avoid overheating of tissues.

These formidable challenges cannot be overcome unless a major paradigm shift in networking through body tissues is made to address the limitations of RF propagation in the human body.

Acoustic waves, typically generated through piezoelectric materials, are known to propagate better than their RF counterpart in media composed mainly of water. Since World War II, piezoelectrically generated acoustic waves have found application, among others, in underwater communications (typically at frequencies between 0 and 100 kHz), in indoor localization in sensor networks, and, massively, in ultrasonic medical imaging. While communication at low frequencies requires sizable transducers, innovations in piezoelectric materials and fabrication methods, primarily driven by the need for resolution in medical imaging, have made micro and nano scale transducers a reality. Moreover, the medical experience of the last decades has demonstrated that ultrasound is fundamentally safe, as long as acoustic power dissipation in tissue is limited to safe levels. It is also known that ultrasonic heat dissipation in tissues is minimal compared to RF waves.

BRIEF SUMMARY OF THE INVENTION

Transmission and medium access control techniques for ultrasonic communication through biological tissue are disclosed. The present invention can be embodied as a method for transmitting data through biological tissue using ultrasonic pulses from a transmitter to a receiver.

In one such embodiment, the method comprises the step of setting, at a transmitter, an initial time-hopping frame length and an initial spreading code length for data transmission. The initial time-hopping frame length and the initial spreading code length may be set based on predetermined values or in vivo values.

The method further comprises the step of sending, from the transmitter, a request-to-transmit packet to a receiver. The request-to-transmit packet may be sent over a control channel at the initial time-hopping frame length and the initial spreading code length. The control channel may be implemented through a time-hopping sequence and a spreading code known by all transmitters and receivers.

The method further comprises the step of receiving, at the transmitter, a clear-to-transmit packet from the receiver. The clear-to-transmit packet may be received over the control channel. The clear-to-transmit packet may comprise feedback information. The feedback information may comprise a measured interference value. In one embodiment, the method further comprises the step of calculating a forward time-hopping frame length and a forward spreading code length based on the measured interference value.

The method further comprises calculating a private time-hopping sequence and private spreading code based on a pseudo-random sequence generator and an ID of the transmitter. The initial and private spreading codes may be based on M-ary PPM-BPSK, M-ary PPM-OOK, M-ary PPM-ASK, M-ary PPM-FSK, M-ary PPM-PPM, or other spreading code type.

The method further comprises establishing a connection with the receiver using the private time-hopping sequence and the private spreading code.

The method further comprises setting, at the transmitter, a forward time-hopping frame length and a forward spreading code length based on the feedback data in the clear-to-transmit packet.

The method further comprises sending, from the transmitter, a data packet using the private time-hopping sequence, private spreading code, forward time-hopping frame length, and forward spreading code length.

The method further comprises receiving, at the transmitter, an acknowledgement packet having updated feedback data. In one embodiment, the updated feedback information may comprise a measured interference value. In such embodiments, the method may further comprise the step of calculating the forward time-hopping frame length and the forward spreading code length based on the measured interference value.

The method further comprises setting, at the transmitter, the forward time-hopping frame length and the forward spreading code length based on the updated feedback information.

In one embodiment, the method may further comprise measuring, at the transmitter, an interference value. In such an embodiment, the data packet may comprise transmitter feedback data based on the measured interference value at the transmitter.

The present invention may also be embodied as a method for receiving transmitted data through biological tissue using ultrasonic pulses.

In one such embodiment, the method comprises receiving, at a receiver, a request-to-transmit packet from a transmitter. The request-to-transmit packet may contain an ID of the transmitter. In one embodiment, the method may further comprise the step of decoding the request-to-transmit packet.

The method further comprises measuring, at the receiver, an interference value. The interference value may be the summation of measured interference and measured noise.

The method further comprises sending, from the receiver, a clear-to-transmit packet to the transmitter. The clear-to-transmit packet comprises feedback data based on the interference value. The clear-to-transmit packet may be transmitted at a predetermined time-hopping frame length and a predetermined spreading code length.

The method further comprises calculating a private time-hopping sequence and private spreading code based on a pseudo-random sequence generator and the ID of the transmitter.

The method further comprises establishing a connection with the transmitter using the private time-hopping sequence and the private spreading code.

The method further comprises receiving, at the receiver, a data packet from the transmitter using the private time-hopping sequence, the private spreading code.

The method further comprises measuring, at the receiver, an updated interference value.

The method further comprises sending, from the receiver, an acknowledgement packet in response to the received data packet. The acknowledgement packet may comprise updated feedback data based on the updated interference value.

Each packet (acknowledgement, data, request-to-transmit, and clear-to-transmit, etc.) may contain a synchronization preamble. The synchronization preamble may comprise a pseudo-random noise sequence of variable length or a chirp sequence of variable length. In one embodiment, the method further comprises correlating the received packet with the synchronization preamble to identify a starting point of the packet.

In one embodiment, the method may further comprise calculating a forward time-hopping frame length and a forward or updated spreading code length based on the measured or updated interference value. Data packets may be sent using the forward time-hopping frame length and the forward spreading code length. The clear-to-transmit packet may comprise the calculated forward time-hopping frame length and the calculated forward spreading code length. The acknowledgement packet may comprise the updated time-hopping frame length and the updated spreading code length.

The present invention may also be embodied as a device for receiving transmitted data through biological tissue using ultrasonic pulses. In one embodiment, such a device comprises a physical layer and a media access control layer.

The physical layer may comprise a preamble detector in electronic communication with an analog-to-digital converter, an interference estimator in electronic communication with the analog-to-digital converter, a pulse correlator in electronic communication with the preamble detector and the interference estimator, a time-hopping deframer in electronic communication with the pulse correlator and the interference estimator, and a code despreader in electronic communication with the time-hopping deframer. In one embodiment, the preamble detector may comprise a single-rate FIR filter used as a correlator, a squaring module, an integrator, and a threshold-based plateau detector. In another embodiment, the physical layer may further comprises a group of externally-accessible settings registers used to reconfigure physical layer parameters.

The medium-access-control layer may comprise a finite state machine receiver. The finite state machine receiver may be in electronic communication with the interference estimator and the code despreader. In one embodiment, the finite state machine receiver may detect a received packet based on information from the preamble detectors. In another embodiment, the finite state machine receiver may decode the received packet based on the output of the physical layer operations. In one embodiment, the finite state machine receiver may estimate the level of interference, and accordingly chooses a time-hopping frame length and a spreading code length.

The present invention may also be embodied as a transmitter for sending data through biological tissue using ultrasonic pulses. In such embodiments, the transmitter comprises a symbol mapper module, a code spreader module in electronic communication with the symbol mapper module, a time-hopper module in electronic communication with the code spreader module, a pulse shaping module in electronic communication with the time-hopper module, and a digital-to-analog converter in electronic communication with the pulse shaping module.

In one embodiment, the symbol mapper module may transform information into M-ary symbols. In another embodiment, the code spreader module may distribute the M-ary symbols into chips based on a pseudo-random spreading code. In one embodiment, the time-hopper module spreads the chips in time according to a selected time-hopping pattern. In another embodiment, the pulse shaping module maps the chips to position-modulated pulses, creating a train of position-modulated pulses following a predefined time-hopping pattern.

In another embodiment, the pulse shaping module may comprise a finite impulse response filter whose coefficients represent the samples of an nth-order derivative gaussian pulse or a chirp sequence.

The present invention may also be embodied as a data or packet structure for communication through biological tissue using ultrasonic pulses. The data or packet structure comprises a packet synchronization preamble, a time-hopping synchronization preamble, a packet header, a packet payload, and a checksum value. The packet header may comprise a start packet delimiter, a packet size value, a packet type value, a transmitter ID, a receiver ID, a time-hopping frame length feedback value, and a spreading code length feedback value.

By recognizing the limitations of traditional radio-frequency wireless communications in interconnecting devices within the human body, the present invention may incorporate network protocols for implantable devices based on ultrasonic transmissions. In this application the feasibility of using ultrasonic waves in human body tissues is assessed. An accurate channel model is derived for ultrasonic intra-body communications. Then, ultrasonic transmission and multiple access techniques are disclosed. One such embodiment will be referred to as Ultrasonic WideBand (UsWB). UsWB is based on the idea of transmitting information bits spread over very short pulses following a time-hopping pattern. The short impulse duration results in limited reflection and scattering effects, and its low duty cycle reduces the impact of thermal and mechanical effects, that are detrimental for human health.

One embodiment of the present invention is a transmission and medium access control (MAC) technique for an ultrasonic BAN or BSN. In UsWB, distributed MAC coordination is achieved by exchanging information on logical control channels, while data packets are transmitted over logical data channels. One embodiment of the invention is includes a BAN or BSN comprising a plurality of implanted sensor nodes operating according to the inventive process. The nodes may be transmitter-receiver pairs or transceivers. In a transmitter-receiver pair or a transceiver, the data may be transmitted by the transmitter to its receiver and sent to an external monitoring device and/or to an actuator by the receiver. Furthermore, one embodiment of the invention is a non-transitory computer-readable medium having stored thereon computer executable code, which, when executed, causes a computing unit to perform methods of the present invention. Throughout the application, the term "transmitter-receiver pairs" includes transceivers.

Embodiments of the present invention may use multiple access techniques with distributed control to enable efficient simultaneous access by mutually interfering devices based on minimal and localized information exchange and on measurements at the receiver only. The application also discusses performance of UsWB through a multi-scale simulator that models the proposed communication system at the acoustic wave level, at the physical (bit) level, and at the network (packet) level.

This application also discusses ultrasound propagation and layers of the protocol stack. Ultrasonic propagation in tissues is discussed. And important tradeoffs, including the choice of a transmission frequency, transmission power, bandwidth, and transducer size is explored.

Embodiments of the present invention may use ultrasonic channel modeling. Channel models for ultrasonic communication in the human body are disclosed herein. The inhomogeneity of the human body, characterized by a multitude of very small organs and tissues, causes severe multipath effect. Reflectors and scatterers cause numerous delayed versions of the transmitted signal to reach the receiver, thus making detection and decoding a challenging operation. In addition, the low speed of sound in tissues leads to high delays that need to be considered in system design.

To address the severe effect of multipath, a transmission and multiple access technique is disclosed. For example, UsWB is based on the idea of transmitting very short pulses following an adaptive time-hopping pattern. The short impulse duration results in limited reflection and scattering effects, and its low duty cycle reduces thermal and mechanical effects that are detrimental for human health. A variable length spreading code is superimposed to the time-hopping pattern to further combat the effect of multipath and to introduce waveform diversity among interfering nodes.

One embodiment of the present invention regulates the data rate of each transmitter to adapt to the current level of interference by distributively optimizing the code length and duration of the time hopping frame. One such embodiment is effective in adapting the network throughput to the current level of interference based on minimal and localized information exchange.

Also presented are performance evaluations for UsWB through a multi-scale simulator that evaluates the embodiment at three different levels, i.e., (i) at the wave level by modeling ultrasonic propagation through reflectors and scatterers, (ii) at the bit level by simulating in detail the proposed ultrasonic transmission scheme, (iii) at the packet level by simulating networked operations and distributed control and adaptation to evaluate metrics such as network throughput and packet drop rate.

DESCRIPTION OF THE DRAWINGS

For a fuller understanding of the nature and objects of the invention, reference should be made to the following detailed description taken in conjunction with the accompanying drawings, in which.

DETAILED DESCRIPTION OF THE INVENTION

Ultrasonic Propagation in Human Tissues

Ultrasonic waves originate from the propagation of mechanical vibrations of particles in an elastic medium at frequencies above the upper limit for human hearing, i.e., 20 kHz. Even if each particle oscillates around its rest position, the vibration energy propagates as a wave traveling from particle to particle through the material. Acoustic propagation through a medium is governed by the acoustic wave equation (referred to as the Helmhotz equation), which describes pressure variation over the three dimensions, $$\nabla^2 P - \frac{1}{c^2}\frac{\partial^2 p}{\partial t^2} = 0, \qquad (1)$$

where P(x, y, z, t) represents the acoustic pressure scalar field in space and time, and c is the propagation speed in the medium with a typical value of 1500 m/s in blood (i.e., five orders of magnitude slower than RF propagation in air).

When ultrasonic waves propagate through an absorbing medium, the initial pressure, $P_0$ reduces to P(d) at a distance d as $$P(d)=P_0 e^{-\alpha d} \qquad (2)$$

where α ([Np·cm$^{-1}$]) is the amplitude attenuation coefficient that captures energy dissipation from the ultrasonic beam and is a function of the carrier frequency f as $\alpha = a f^b$, where a([Np·m$^{-1}$ MHz$^{-b}$]) and b are tissue attenuation parameters.

TABLE 1

| Frequency Limits for A = 100 dB | | |
|---|---|---|
| Communication Range | Distance | Frequency Limit |
| Short Range | μm-mm | >1 GHz |
| Medium Range | mm-cm | ≈100 MHz |
| Long Range | >cm | ≈10 MHz |

Attenuation can be significant, and attenuation may increase with the distance between transmitter and receiver. Moreover, the beam spread is inversely proportional to the ratio between the diameter of the radiating surface and the wavelength of the operating frequency. Consequently, since most biomedical sensing applications require directional transducers, one needs to operate at high frequencies to keep the transducer size small. However, as expected, higher frequencies lead to higher attenuation.

Figure 1:
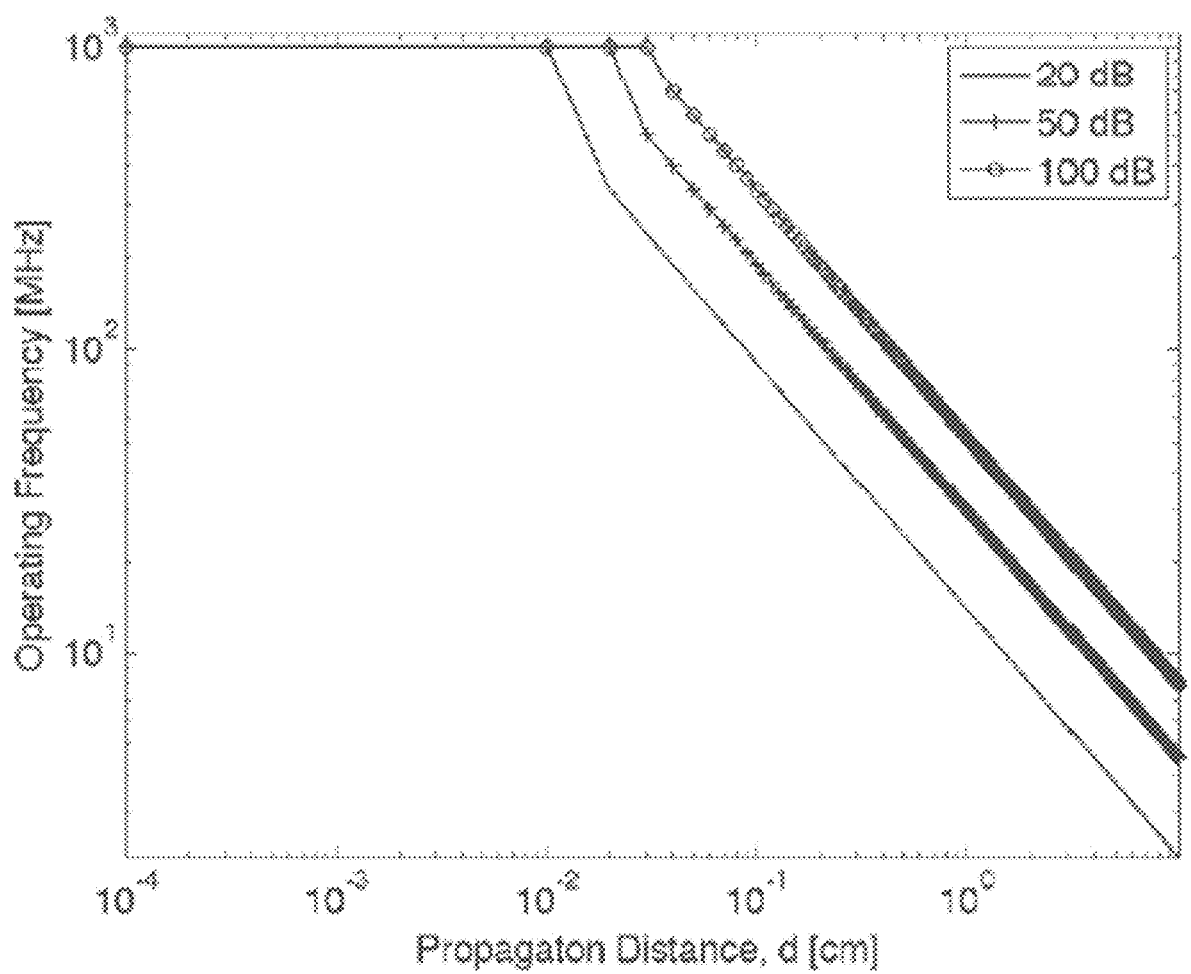
FIG. 1 is a graph showing operating frequency as a function of the propagation distance, with varying levels of tolerable attenuation.

In FIG. 1, the maximum "allowed" carrier frequency is shown with respect to distance, for different values of the maximum tolerable attenuation. Blood is considered as the propagation medium and the maximum operating frequency is limited to 1 GHz. In Table 1, findings are summarized on the maximum "allowed" carrier frequency for a 100 dB maximum tolerable attenuation. For distances ranging between some μm up to a few mm (i.e., short range communications) frequencies higher than 1 GHz can be used. When distances are higher than 1 mm but still lower than some cm, i.e., for medium range communications, the transmission frequency should be decreased to approximately 100 MHz. For distances higher than a few cm, i.e., for long range communications, the transmission frequency should not exceed 10 MHz.

Considerations in determining the operating frequency may include (i) the frequency dependence of the attenuation coefficient, and (ii) the frequency dependence of the beam spread of ultrasonic transducers (which is inversely proportional to the ratio of the diameter of the radiating surface and the wavelength). Therefore, higher frequencies help keep the transducer size small, but result in higher signal attenuation. Since most biomedical sensing applications require directional transducers, one needs to operate at the lowest possible frequencies compatible with small-size transducers and required signal bandwidth. For propagation distances in the order of several cm the operating frequency should not exceed 10 MHz.

The human body is composed of different organs and tissues with different sizes, densities and sound speeds. Therefore, it can be modeled as an environment with pervasive presence of reflectors and scatterers. The direction and magnitude of the reflected wave depend on the orientation of the boundary surface and on the acoustic impedance of the tissues, while scattered reflections occur when an acoustic wave encounters an object that is relatively small with respect to its wavelength or a tissue with an irregular surface. Consequently, the received signal is obtained as the sum of numerous attenuated, possibly distorted, and delayed versions of the transmitted signal.

Channel Modeling

Propagation of acoustic waves through biological tissues is governed by three coupled first-order equations, i.e., the continuity equation, the force equation and the equation of state, which represent relationships among acoustic pressure, P, acoustic particle velocity u, and medium density $\rho$, and can be rearranged to obtain the Helmhotz equation. A realistic channel model of ultrasonic signal propagation in human tissues incorporates all the aspects discussed above including attenuation, scattering and multipath needs to satisfy the three above equations simultaneously. The solution represents the acoustic field propagation in space and time.

Traditionally, partial differential equations are solved using numerical methods such as the finite-difference-method (FDM). However, a computationally more efficient approach may be taken based on the pseudo-spectral and k-space methods. Basically, the pseudo-spectral (PS) method reduces computational complexity in the spatial domain by using Fourier series expansions and FFTs, while the k-space method operates in the time domain by using k-space propagator functions (instead of classical finite differences) to approximate temporal derivatives. As a consequence, larger time steps can be used, reducing the simulation time with controllable accuracy. One tool implementing this method is k-Wave.

Figure 2:
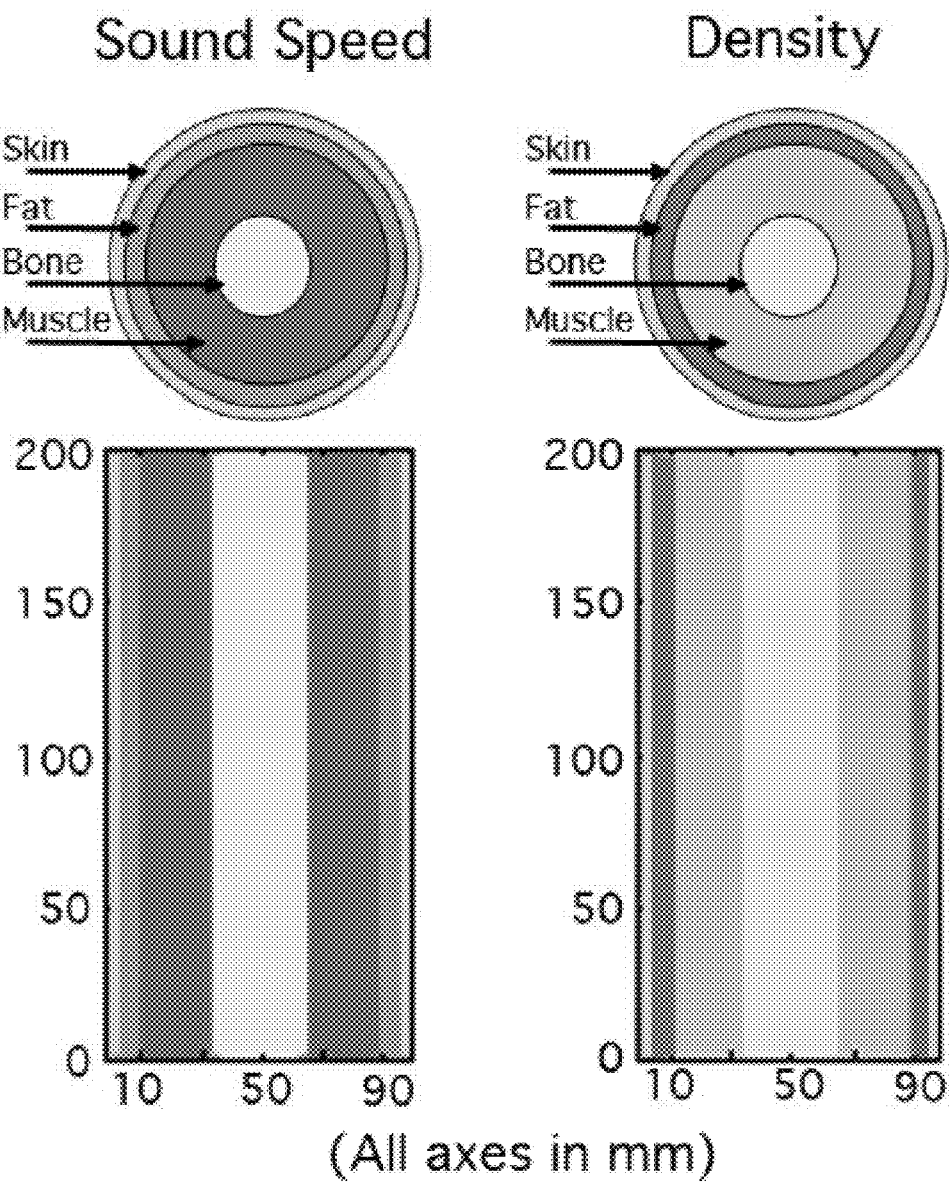
FIG. 2 is a diagram showing sound speed and density distributions in a modeled human arm.

A reference ultrasonic propagation channel was modeled in the human body to derive an accurate characterization of the channel impulse response, which was then used in PHY and MAC layer simulation studies. Specifically, a section of the human arm was modeled, including bones, muscles, fat and skin. A heterogeneous two-dimensional rectangular area of length 20 cm and width 10 cm was considered, where density and sound velocity are distributed as shown in FIG. 2. The bone half-section has a 18 mm width, the muscle half-section has a 22 mm width, while fat and skin have a half-section of 7 mm and 3 mm width, respectively. The medium parameters, sound speed c, density $\rho$ and attenuation a are as in Table II. The attenuation parameter b is set to 1 for all considered tissues.

Figure 3:
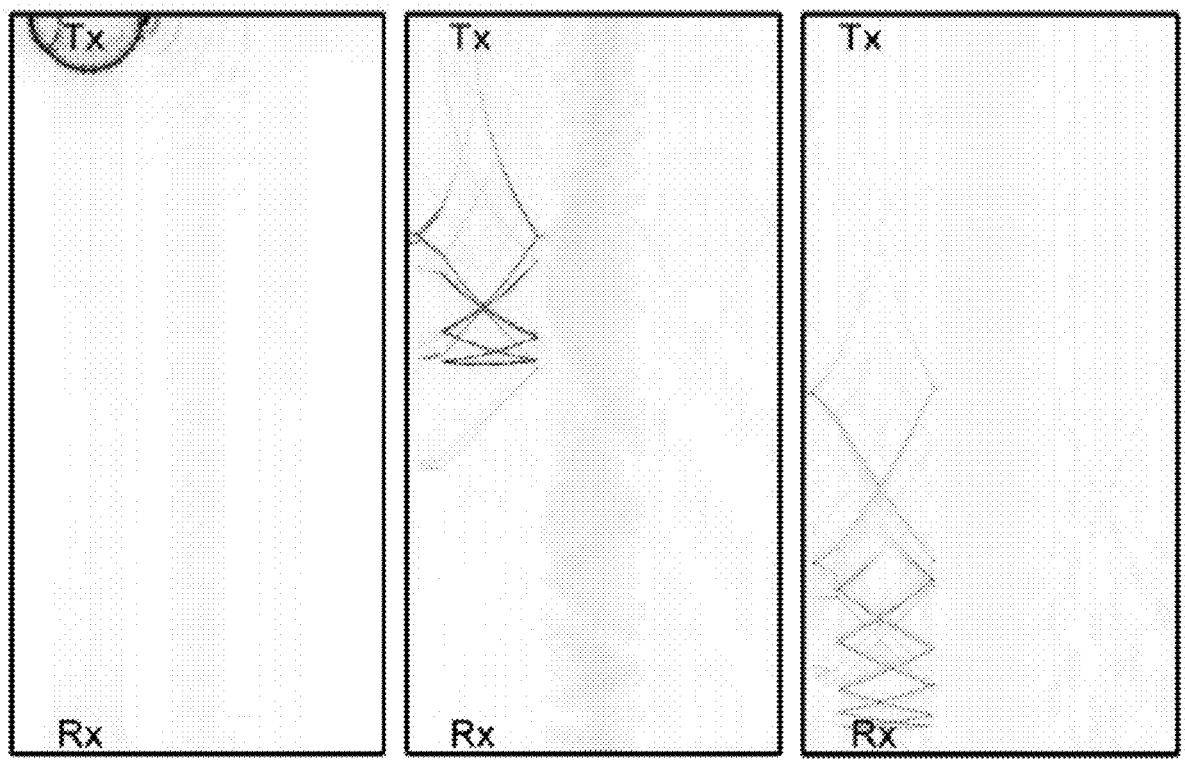
FIG. 3 shows multiple images of the time evolution of an acoustic field in the modeled human arm of FIG. 2.

The channel impulse response was obtained by releasing an ideal Dirac pulse in the left top corner of the muscle section. The receiver is located in the left bottom corner of the muscle section. The transmitter and receiver are located 20 cm away from one another. In FIG. 3, snapshots are shown of the acoustic field time propagation in the modeled environment. The effect of the bone and tissues partially reflects and scatters the acoustic wave transmitted by the source. A channel impulse response is obtained by recording the time series of the signal at the receiver sensor.

TABLE 2

Tissue Parameters

| Tissue | C [m/s] | P [Kg/m³] | $\alpha$ ([Np · m⁻¹ MHz⁻ᵇ]) |
|---|---|---|---|
| Bone | 2407 | 1920 | 1.8 |
| Muscle | 1629 | 1056 | 0.125 |
| Fat | 1487 | 939 | 0.093 |
| Skin | 1729 | 1190 | 0.212 |

Figure 4:
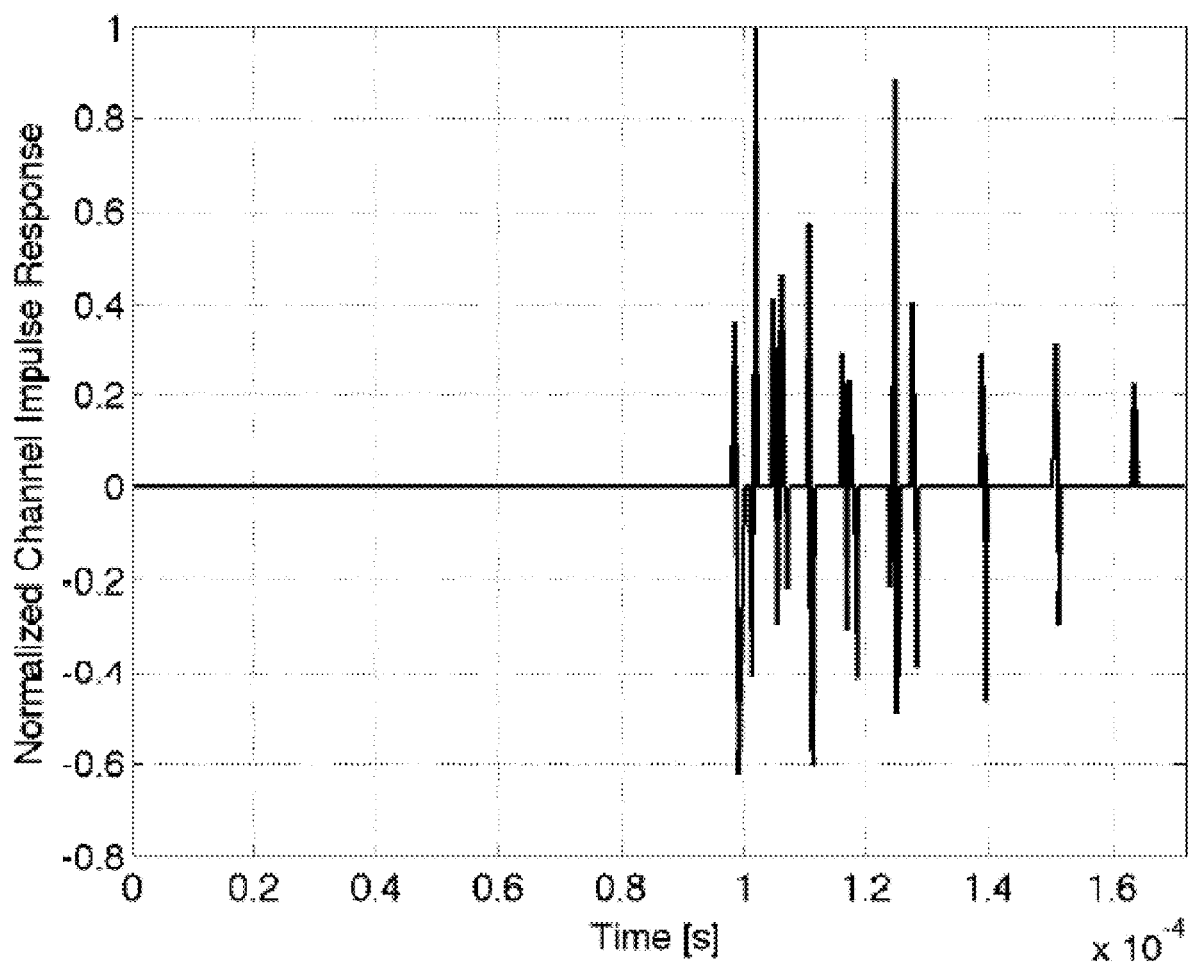
FIG. 4 is a graph showing an ultrasonic channel impulse response in the modeled human arm of FIG. 2.

FIG. 4 shows the resulting impulse response in this scenario. The effect of multipath and scattering introduces attenuated signal replicas spaced in time. Because of the very short duration of the transmitted pulses, replicas do not interact destructively. As such, the channel response can be modeled as a complex-valued low-pass equivalent impulse response, as $h(\tau, t) = \Sigma_{k=1}^{K} a_k(t)\delta(\tau-\tau_k)e^{j\theta_k(t)}$ where $\delta$ is the Dirac delta function, K is the number of resolvable multipath components, $\tau_k$ is the delay of the multipath components, $a_k$ is the path amplitude value and $\theta_k$ is the path phase value. With this description, the channel can be characterized through the mean excess delay ($\tau_m$) and the RMS delay spread ($\tau_{RMS}$). For the channel simulated above, $\tau_m = 4.4353 \cdot 10^{-6}$ s and $\tau_{RMS} = 2.3389 \cdot 10^{-6}$ s. Since the coherence bandwidth of the channel is proportional to the inverse of $\tau_{RMS}$, the should be considered channel as frequency selective for signals of bandwidth above approximately 85 kHz.

Figure 5:
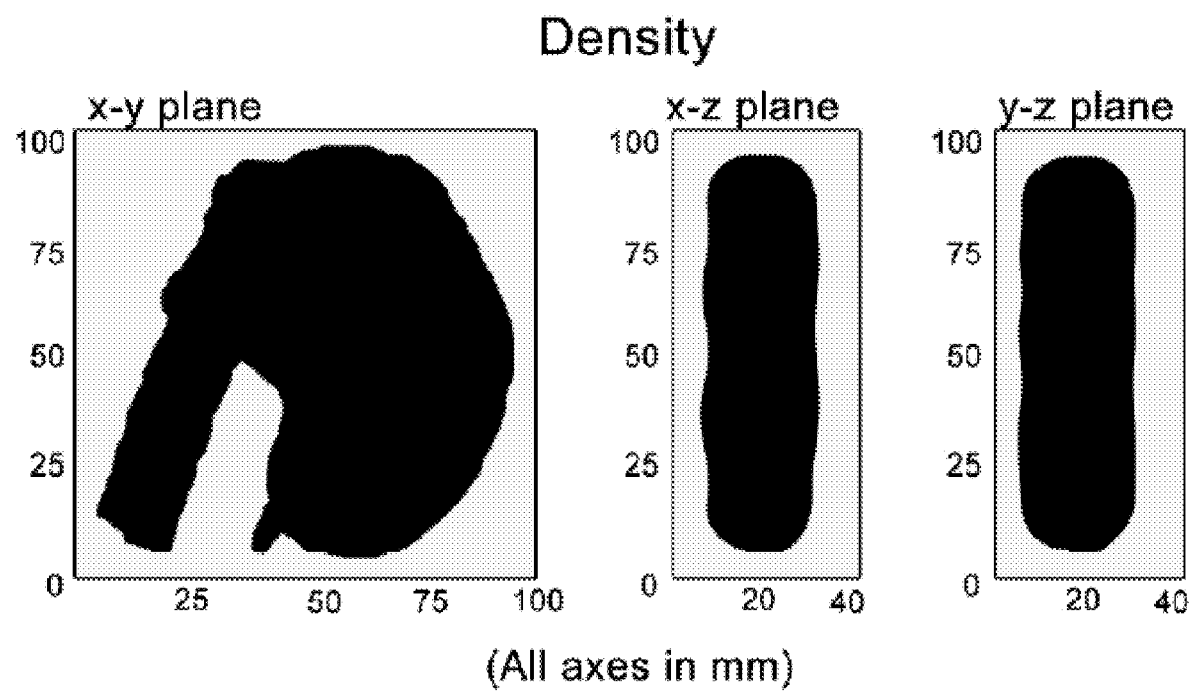
FIG. 5 shows multiple images of the density distributions in a modeled human kidney.
Figure 6:
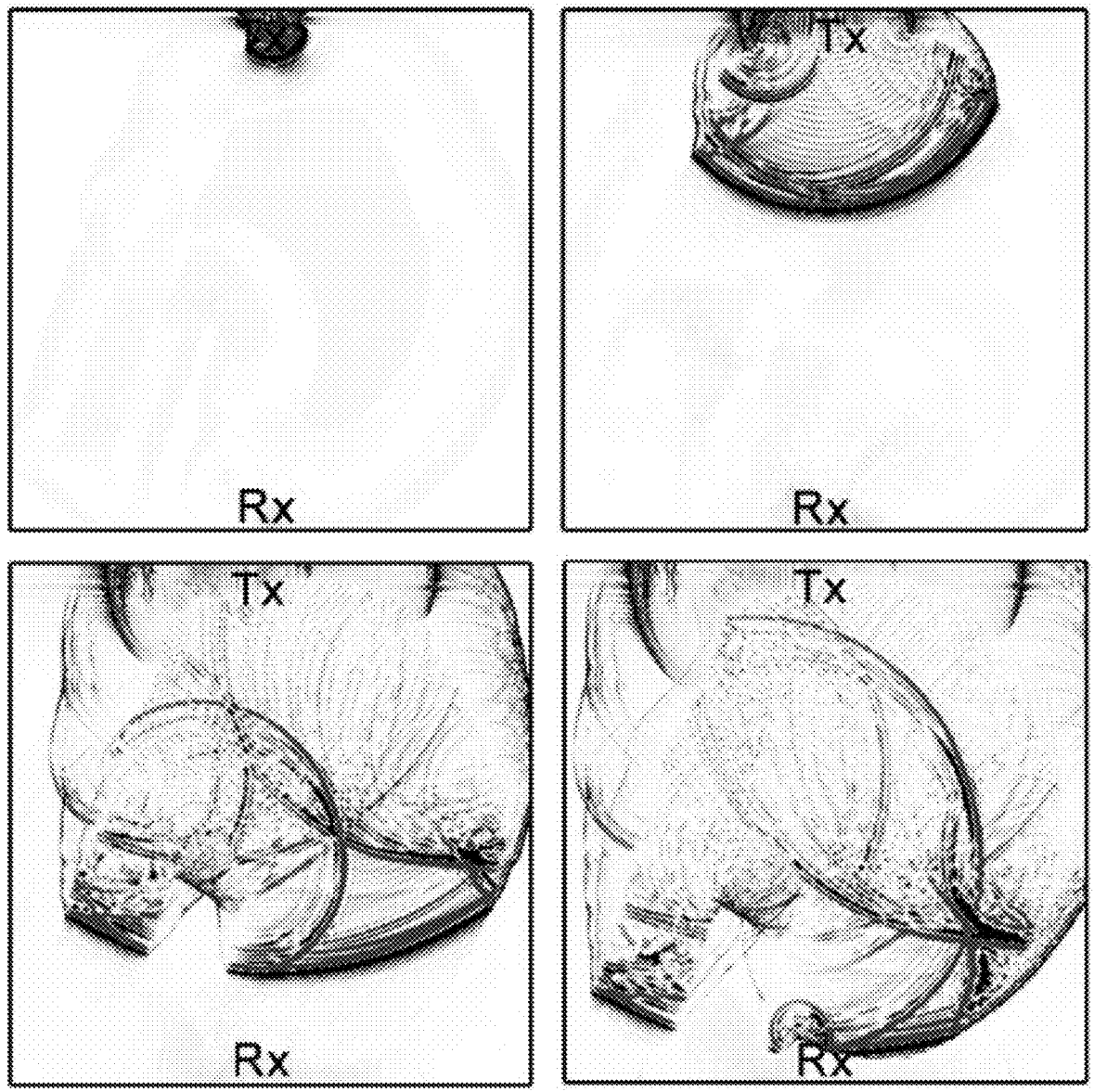
FIG. 6 shows multiple images of the time evolution of the acoustic field in the modeled 2D human kidney of FIG. 5.
Figure 7:
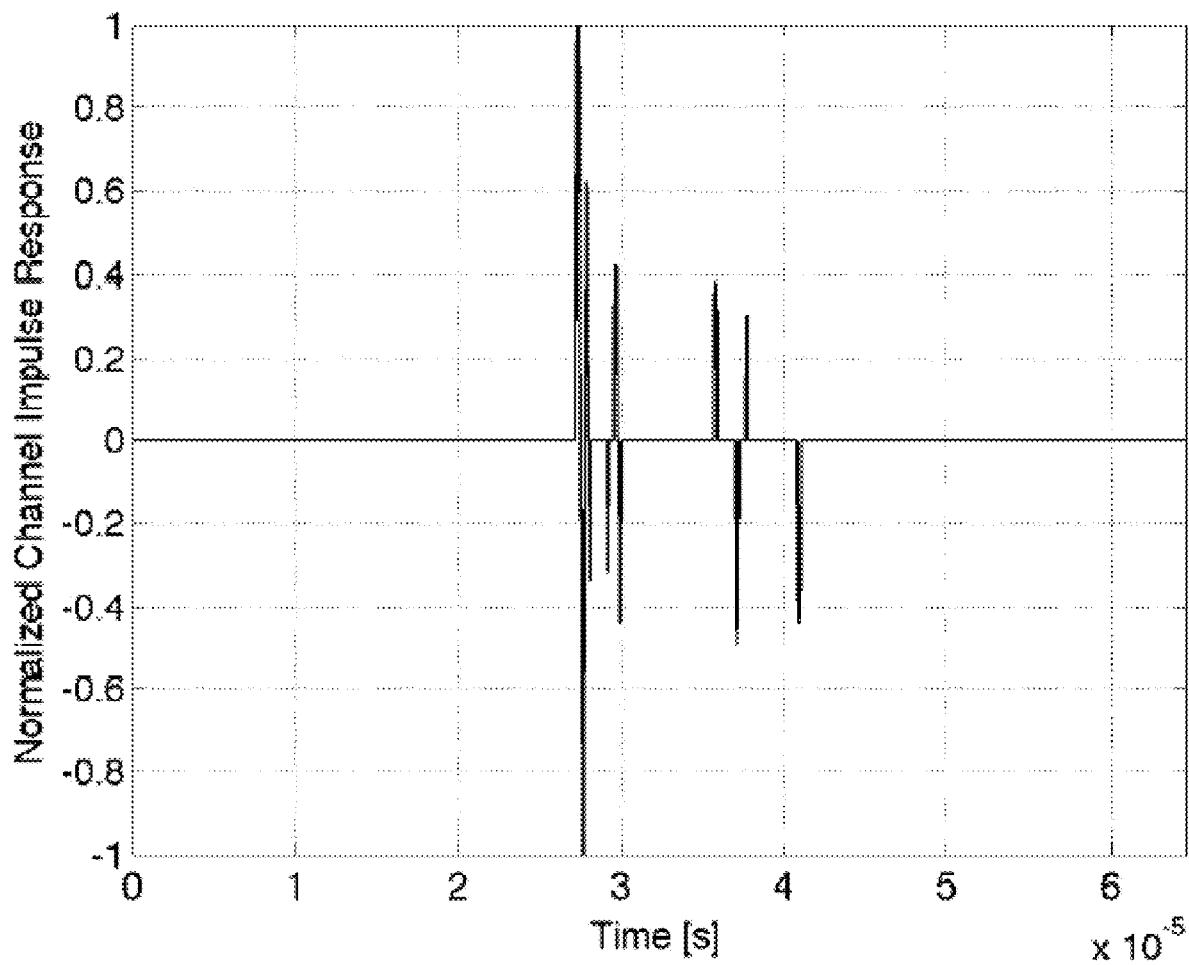
FIG. 7 is a graph showing an ultrasonic channel impulse response in the modeled human kidney of FIG. 5.
Figure 8:
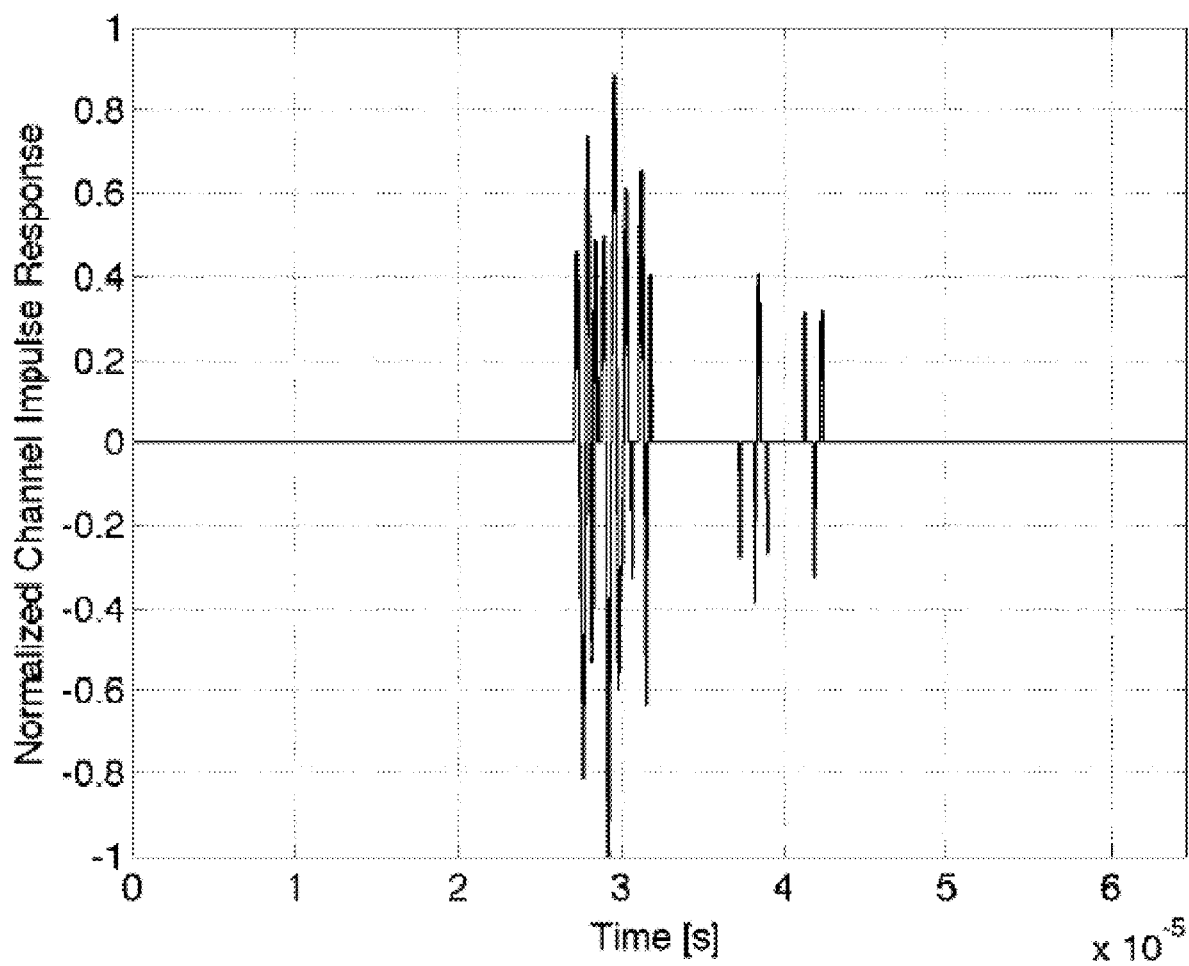
FIG. 8 is a graph showing a second ultrasonic channel impulse response in the modeled 3D human kidney of FIG. 5.

A three-dimensional human kidney was also modeled enclosed in a background medium with similar density and speed of sound. This model accurately reproduces the characteristic of a commercial acoustic phantom mimicking the propagation characteristic of human kidney. The background medium has very low attenuation coefficient, i.e., it is almost transparent for ultrasonic propagation. The medium parameters, sound speed c, density $\rho$ and attenuation a are as in Table III. In FIG. 5, the density distribution is shown in the three section planes, with each plane crossing the kidney in the middle. The simulation discussed above was repeated in the two-dimensional section of the kidney that lays on the x-y plane. Again, the channel impulse response was obtained by releasing an ideal Dirac pulse at the top side of the kidney, while the receiver is located 10 cm down at the bottom. In FIG. 6, four snapshots are of the ultrasonic wave propagation are shown, and the result of the pulse propagation is shown in FIG. 7. Since the medium is more homogeneous than in the previous case, the channel impulse response presents a reduced number of pulse replicas and a more regular attenuation pattern. By characterizing the channel response as a complex-valued low-pass equivalent impulse response, $\tau_m = 1.8214 \cdot 10^{-6}$ s and $\tau_{RMS} = 2.0378 \cdot 10^{-6}$ s. The coherence bandwidth of the channel is around 100 kHz. The same simulation was repeated considering a three dimensional setup, and assuming that the pulse transmitter is located at the top side of the kidney in the x-y plane, and in the middle of the x-z and y-z planes. The resulting pulse propagation is shown in FIG. 8. The third dimension increases the number of replicas of the signal that reach the receiver, therefore the complex-valued low-pass equivalent impulse response parameter become $\tau_m = 8.8256 \cdot 10^{-6}$ s and $\tau_{RMS} = 1.3924 \cdot 10^{-6}$ s. The coherence bandwidth of the channel is in this case 140 kHz.

TABLE 3

Tissue Parameters

| Tissue | C [m/s] | P [Kg/m³] | α ([Np · m⁻¹ MHz⁻ᵇ]) |
|---|---|---|---|
| Kidney | 1550 | 1030 | 0.046 |
| Background Gel | 150 | 1020 | 0.011 |

Ultrasonic Wideband

Some design objectives of UsWB include: (1) to enable low-complexity and reliable communications in ultrasonic channels against the effect of multipath reflections within the human body; (2) to limit the thermal effect of communications, which is detrimental to human health; and (3) to enable distributed medium access control and rate adaptation to combat the effect of interference from co-located and simultaneously transmitting devices.

UsWB can provide physical layer functionalities and medium access control arbitration and adaptation to enable multiple concurrent co-located transmissions with minimal coordination. UsWB transmits short information-bearing carrierless ultrasonic pulses, following a pseudo-random adaptive time-hopping pattern with a superimposed spreading code of adaptive length. Impulsive transmission and spread-spectrum encoding combat the effects of multipath and scattering and introduce waveform diversity among interfering transmissions.

Ultrasonic Pulsed Transmissions. Ultrasonic wideband transmits very short ultrasonic pulses following an adaptive time-hopping pattern together with a superimposed adaptive spreading code. Baseband pulsed transmissions enable high data rate, low-power communications, low-cost transceivers.

The characteristics of pulsed transmissions appear to advantageously address the requirements discussed above. Their fine delay-resolution properties are well-suited for propagation in the human body, where inhomogeneity in terms of density and propagation speed, as well as the pervasive presence of very small organs and particles, cause dense multipath and scattering. When replicas of pulses reflected or scattered are received with a differential delay at least equal to the pulse width, they do not overlap in time with the original pulse. Therefore, for pulse durations in the order of hundreds of nanoseconds, pulse overlaps in time are reduced and multiple propagation paths can be efficiently resolved and combined at the receiver to reduce the bit error rate. Also, the low duty cycle of pulsed transmissions reduces the impact of thermal and mechanical effects, which are detrimental for human health. Observe also that the large instantaneous bandwidth enables fine time resolution for accurate position estimation and network synchronization. Finally, interference mitigation techniques may enable MAC protocols that do not require mutual temporal exclusion between different transmitters. This is relevant in the ultrasonic transmission medium since the propagation delay is five orders of magnitude higher than in RF in-air channels and carrier-sense-based medium access control protocols are ineffective. In addition, data rate can be flexibly traded for power spectral density and multipath performance.

Physical Layer Model

Adaptive Time-Hopping. Consider a slotted time divided in chips of duration $T_c$, with chips organized in frames of duration $T_f = N_h \cdot T_c$, where $N_h$ is the number of chips, i.e., slots, per frame. Unless otherwise specified, the frame and spreading code length are assumed to be the same for all nodes, and are simply denoted as $N_h$ and $N_s$. $N_h$ is the frame code length, i.e., number of chips per frame, and $N_s$ is the spread code length.

Each user transmits one pulse in one chip per frame, and determines in which chip to transmit based on a pseudo-random time hopping sequence (THS), i.e., a sequence generated by seeding a random number generator with the user's unique ID.

The train of pulses is modulated based on pulse position modulation (PPM), i.e., a '1' symbol is carried by a pulse delayed by a time δ with respect to the beginning of the chip, while a '0' symbol begins with the chip. The signal $s^{(k)}(t, i)$ generated by the $k^{th}$ user to convey the $i^{th}$ symbol is expressed as $$s^{(k)}(t,i) = p(t - c_i^{(k)} T_c - i T_f - d_i^{(k)} \delta) \quad (3)$$

where p(t) is the second derivative of a Gaussian Pulse, $\{c_i^{(k)}\}$ is the time hopping sequence of the $k^{th}$ source, with $0 \le c_i^{(k)} \le N_h - 1$, and $\{d_i^{(k)}\}$ is the information-bearing sequence, $d_i^{(k)} \in \{0,1\}$. The resulting data rate, in pulses per second, is expressed as:

$$R(N_h) = \frac{1}{T_f} = \frac{1}{N_h T_c}. \quad (4)$$

By regulating the time-hopping frame length $N_h$, i.e., the average inter-pulse time, a user can adapt its transmission rate, and as a consequence modify the average radiated power and therefore the level of interference generated to other ongoing communications. An individual user has little incentive to increase its frame size, since that results in a lower achievable data rate, without any major benefit for the user itself (since the level of interference perceived depends primarily on the frame length of the other users, and not on its own). However, a longer time frame reduces the interference generated to the other users. Therefore, selfish/greedy frame adaptation strategies do not work well in this context and cooperative strategies are needed.

At the receiver, frame synchronization and "time hopping" synchronization must be performed to properly decode the received signal. Frame synchronization comprises finding the correct time alignment between the transmitter frame and the receiver frame. In general, this can be achieved through an energy-collection approach. During the frame synchronization, the transmitter sends an a-priori-known sequence, i.e., a preamble. After correlating the received signal and the expected signal, the receiver identifies the starting point of the frame as the time instant where the correlation is maximized. The second step consists of finding the time-hopping sequence to hop chip-by-chip and correlate the received pulses. This can be achieved by seeding the random generator with the same seed used by the transmitter, and therefore generating the same pseudo-random time-hopping sequence.

Once both synchronization processes have been accomplished, the receiver can decode the received signal by "listening" in the time chips of interests and correlating the received pulse according to the modulation scheme in use.

Adaptive Channel Coding. An adaptive channel code reduces the effect of mutual interference from co-located devices, by dynamically regulating the coding rate to adapt to channel conditions and interference level. Various channel coding solutions are available with different performance levels and computational complexity. In one embodiment, simple pseudo-orthogonal spreading codes are used because of their multiple access performance, limited computational complexity, and inherent resilience to multipath. Each symbol (i.e., bit) is spread by multiplying it by a pseudorandom code before transmission. At the receiver side, with prior knowledge of the code used at the transmitter, the signal can be de-spread, and the original information recovered. With different orthogonal (or pseudo-orthogonal) codes, multiple nodes can transmit simultaneously on the same portion of the spectrum, with reduced interference. Two alternative modulation schemes are presented, which are referred to as PPM-BPSK-spread and PPM-PPM-spread.

In PPM-BPSK-spread, the binary spreading code at the $k^{th}$ node, $\{a_j^{(k)}\}$, is defined as a pseudorandom code of $N_s$ chips with $a_j \in \{-1, 1\}$. Accordingly, the information bit is spread using BPSK modulated chips, and by combining with time hopping, (3) can be rewritten as $$s^{(k)}(t,i) = \Sigma_{j=0}^{N_s-1} a_j^{(k)} p(t - c_j^{(k)} T_c - jT_f - d_i^{(k)} \delta) \quad (5)$$

where $\delta$ is the PPM displacement of a pulse representing a '1' bit, while chip information is carried in the pulse polarity. In PPM-PPM-spread, the information bit is spread using PPM-modulated chips. In this case, the binary spreading code can be defined as a pseudorandom code of $N_s$ chips with $a_j \in \{0, 1\}$. With time hopping, (3) can be rewritten as $$s^{(k)}(t,i) = \Sigma_{j=0}^{N_s-1} p(t - c_j^{(k)} T_c - jT_f - (a_j^{(k)} \oplus d_i^{(k)}) \delta) \quad (6)$$

where $\oplus$ represents the XOR operation.

Figure 9:
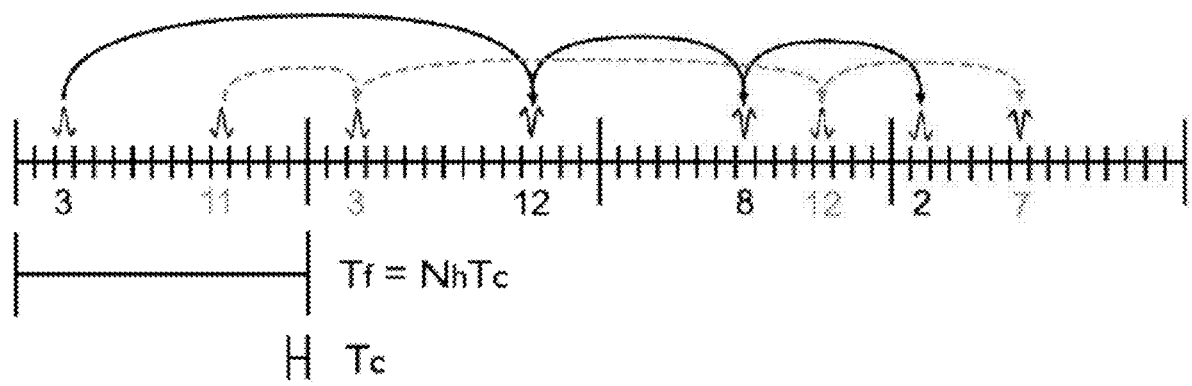
FIG. 9 is a chart showing an example of two ongoing transmissions using time hopping sequences according to one embodiment of the present invention.

In FIG. 9, an example of a combined time hopping and PPM-BPSK-spread coding strategy is shown. Since the spreading operation associates $N_s$ chips to one information bit, the information rate will be further reduced by a factor $N_s$, i.e., $$R(N_h, N_s) = \frac{1}{N_s T_f} = \frac{1}{N_s N_h T_c} \quad (7)$$

while the energy per bit is increased by a factor $N_s$. Note that there is a tradeoff between robustness to multi-user interference (which increases with longer spreading codes), and energy consumption and information rate. In both cases, PPM-PPM-spread and PPM-BPSK-spread, the receiver can employ the spreading code employed at the transmitter to obtain the correlator template. With BPSK-modulated chips the absolute received phase information is needed for decoding. Therefore, a coherent receiver with accurate channel knowledge is needed. Instead, with a pure PPM-modulated signal, a simple non-coherent energy detector receiver is sufficient. The latter requires frame synchronization only, and its hardware complexity is significantly lower.

Signal to Interference-plus-Noise Ratio. The signal to interference-plus-noise ratio (SINR) for impulsive transmissions at the receiver of link i can be expressed as $$SINR_i(N_h, N_s) = N_{s,i} \frac{P_i g_{i,j} N_{h,i} T_c}{\eta + \sigma^2 T_c \sum_{k \in I_i} P_k g_{k,i}} \quad (8)$$

where $P_i$ is the average power per pulse period emitted by the $i^{th}$ transmitter, $g_{i,j}$ is the path gain between the $i^{th}$ transmitter and the $j^{th}$ receiver, $\eta$ represents background noise energy and $\sigma^2$ is an adimensional parameter depending on the shape of the transmitted pulse and the receiver correlator. The set $I_i$ represents the set of links whose transmitter interferers with the receiver of link i. $T_f = N_h T_c$ is the frame duration. When different links use different frame lengths, (8) becomes $$SINR_i(N_h, N_s) = N_{s,i} \frac{P_i g_{i,j} N_{h,i} T_c}{\eta + \sigma^2 T_c \sum_{k \in I_i} \frac{N_{h,i}}{N_{h,k}} P_k g_{k,i}}. \quad (9)$$

The expression in (9) depends on the array of frame and code lengths of all the ongoing communications in the network, i.e., $N_h$, $N_s$, whose $i^{th}$ elements are $N_{h,i}$ and $N_{s,i}$, respectively. The term $$\frac{N_{h,i}}{N_{h,k}}$$

accounts tor me level of interference generated by each interferer k to the receiver of link i, i.e., the number of pulses transmitted by the $k^{th}$ transmitter during the time frame of the $i^{th}$ user. Note that power control strategies are not considered since, in the linear regime, when the objective is to maximize the aggregate data rate, the optimal solution always corresponds to points where individual devices transmit at the maximum power, or do not transmit at all.

Note that increasing (or decreasing) the spreading code length of the node of interest, $N_{s,i}$, leads to an increase (decrease) in the SINR. When the node of interest increases (decreases) its frame length, $N_{h,i}$, while the other nodes do not, no variation in the SINR is expected (there is in fact a slight increase (decrease) in the SINR, which can be neglected under high SNR conditions, $\eta \ll \Sigma_{k \in I_i} P_k g_{k,i}$).0 Finally, when the frame length of the interfering nodes is increased (decreased), the SINR increases (decreases).

Bit Error Rate. The bit error rate at the receiver can be approximated by evaluating the pulse collision probability when time hopping and channel coding are used. Consider first a pure time-hopping system with no pulse repetition, i.e., one transmitted pulse per bit. Assume that the information carried by a pulse cannot be decoded correctly only if two or more pulses from different users, representing different symbols, are transmitted in the same time chip. Under this hypothesis, considering K interferers using the same frame length $N_h$, the probability of collision is given by $$P_c = 1 - \Sigma_{i=0}^{|M|-1} p_i \left[1 - (1-p_i)\frac{1}{N_h}\right]^K, \quad (10)$$

where $p_i$ is the a-priori probability of transmitting the $i^{th}$ symbol in the set of possible symbols M, e.g., $\{0, 1\}$, with $|M|$ the size of the set M, and $$(1-p_i)\frac{1}{N_h}$$

is the probability that one pulse collides (because the symbol is different), that is the information carried by the pulse cannot be decoded correctly.

Since the collision probability depends on the number of pulses transmitted by an interferer within the user time frame, $N_h$ in (10) represents the frame length of the node generating interference. Thus, if different nodes use different frame lengths, (10) can be rewritten as $$P_c = 1 - \sum_{i=0}^{|M|-1} p_i \prod_{j=0}^{G} \left[1 - \frac{(1-p_i)}{N_{h,j}}\right]^{K_j}, \quad (11)$$

where $N_{h,j}$ is the frame length in number of chips used by the $K_j$ nodes in the $j^{th}$ group. G is the number of groups into the network, where each group includes all the nodes in the network using the same frame length.

Finally, we consider the effect of pulse repetition. Assume that, for each bit, $N_s$ pulses are sent, one per each frame. The bit cannot be correctly decoded if more than half of the transmitted pulses collide. Since the probability of having x collisions over $N_s$ transmissions follows as known a binomial distribution $$P_x = \binom{N_s}{x} P_c^x (1 - P_c)^{N_s - x}, \quad (12)$$

the probability that more than half transmitted pulses collide is given by $$P_{\frac{N}{2}+1} = \sum_{k=\lfloor \frac{N_s}{2} \rfloor + 1}^{N_s} P_x, \quad (13)$$

Finally, the symbol error rate can be expressed as:

$$P_{err} = 1 - \sum_{i=0}^{|M|-1} p_i \left[1 - (1-p_i) P_{\frac{N}{2}+1}\right]. \quad (14)$$

Note that this expression is exact for a simple repetition code. A pseudo-random spreading code increases the collision recovery capabilities at the receiver. Thus, the effective BER will be further reduced. The BER is a decreasing function of the code length of the transmission and of the frame length of the interfering nodes. Increasing the code length of the transmission and the frame length of the interfering nodes reduces the probability of collision. Increasing the frame length of the transmitter does not lead to any BER variation.

MAC and Rate Adaptation

In this section, UsWB medium access control principles and rate adaptation are discussed. As mentioned above, there is a tradeoff between (i) resilience to interference and channel errors, (ii) achievable information rate, and (iii) energy efficiency. In this section, medium access control and rate adaptation strategies are disclosed to find optimal operating points along efficiency-reliability tradeoffs.

Distributed Rate-Maximizing Adaptation

One objective of the rate-adaptation algorithms disclosed herein is to let each active communication maximize its transmission rate by selecting a pair of code and frame lengths, based on the current level of interference and channel quality measured at the receiver and on the level of interference to the other ongoing communications generated by the transmitter. In one embodiment, the communication may occur in a decentralized ultrasonic intra-body area network. Denote by $\mathcal{N}$ the set of $|\mathcal{N}|$ existing connections, and by $N_{h,max}$ and $N_{s,max}$ the maximum frame and code lengths supported, $$0 < N_{h,i} \leq N_{h,max}, \forall i \in \mathcal{N}, N_h \in \mathbb{N}, \quad (15)$$

$$0 < N_{s,i} \leq N_{s,max}, \forall i \in \mathcal{N}, N_s \in \mathbb{N}, \quad (16)$$

where $\mathbb{N}$ is the set of natural numbers. According to the transmission scheme discussed above, each node i transmits at a rate $R_i$ expressed as in (7) and each receiver experiences an SINR expressed as in (9). Each node has a minimum data rate requirement, i.e., $R_i(N_{h,i}, N_{s,i}) \geq R_{min}$, and a minimum SINR requirement, i.e., $SINR_i(N_{h,i}, N_{s,i}) \geq SINR_{min}$.

Explicitly Cooperative Problem. The receiver is in charge of estimating the interference and calculating the optimal frame and spreading code lengths that maximize the system performance. Accordingly, the frame length and the code length calculated by the receiver of the connection r, are denoted as $N_{h,r}$ and $N_{s,r}$.

The objective of each user is to locally optimize the information rate of the connection by solving the following problem:

$$\max_{N_{h,r}, N_{s,r}} R_r(N_{h,r}, N_{s,r}) \quad (17)$$

$$\text{subject to } R_r(N_{h,r}, N_{s,r}) \geq R_{min} \quad (18)$$

$$SINR_r(N_{h,r}, N_{s,r}) \geq SINR_{min} \quad (19)$$

$$SINR_i(N_{h,r}, N_{s,r}) \geq SINR_{min} \forall i \in I_r, \quad (20)$$

where $I_r$ is the set of the connections interfering with the $r^{th}$ connection. The constraints on the maximum frame and code length in (15) and (16) are also implicitly considered. This will be referred to as the explicitly cooperative problem.

Implicitly Cooperative Problem. If all nodes measure the same level of interference, that is, all network nodes are close enough to be all in the same transmission range, and all nodes have the same minimum rate and minimum SINR requirements, the level of interference that can be tolerated by each receiver is the same. Therefore, the information about the maximum interference tolerated by each receiver does not need to be exchanged. The problem in (17) becomes then $$\max_{N_{h,r}, N_{s,r}} R_r(N_{h,r}, N_{s,r})$$

$$\text{subject to } R_r(N_{h,r}, N_{s,r}) \geq R_{min} \quad (21)$$

$$SINR_r(N_{h,r}, N_{s,r}) \geq SINR_{min} \quad (22)$$

The system of SINR inequality constraints in (17) becomes here a single inequality constraint. The new problem can be interpreted as finding the optimal pair of code and frame length that maximize the rate, given a minimum rate and a minimum SINR, under the assumption that all the other nodes will be acting in the same way. Since the problem to be solved is the same for each node, a globally optimal pair of code and frame lengths will be found. This is referred to as the implicitly cooperative problem.

The implicitly cooperative problem can be derived as a special case by neglecting the constraint in (20). The explicitly cooperative problem, stated in (17) is an integer program, i.e., variables $N_{h,r}$ and $N_{s,r}$, are integer. If the domain of the problem is small, it can be solved by enumeration, i.e., trying all the possible combinations of $N_{h,r}$ and $N_{s,r}$. When the domain of the problem increases in size, a relaxation method can be used to transform the integer problem into a fractional problem. The relaxation operation consists of replacing the constraints in (15) and (16) with $$0 < N_{h,r} \leq N_{h,max}, 0 < N_{s,r} \leq N_{s,max}, N_{s,r}, N_{h,r} \in \mathbb{R} \qquad (23)$$

where $\mathbb{R}$ is the set of real numbers. Note that the optimal solution to the relaxed problem is not necessarily an integer. However, since the feasible set of the relaxed problem is larger than the feasible set of the original integer program, the optimal value of the former, $p_{rlx}^*$ is a lower bound on the optimal value of the latter, $p_{int}^*$, i.e., $$L = p_{rlx}^* \leq p_{int}^* \qquad (24)$$

The relaxed solution can be used to find an integer solution by rounding its entries based on a threshold $\theta \in [0, 1]$, i.e., $$\hat{x}_{int}^* = \begin{cases} \lceil x_{rlx}^* \rceil & \text{if } \lceil x_{rlx}^* \rceil - x_{rlx}^* \geq \theta \\ \lfloor x_{rlx}^* \rfloor & \text{otherwise} \end{cases} \qquad (25)$$

where $\lceil \cdot \rceil$ and $\lfloor \cdot \rfloor$ are the ceiling and floor functions, respectively. If the rounded solution, $x_{rlx}^*$, is feasible for the original problem, i.e., all the constraints are satisfied, then it can be considered a guess at a good, if not optimal, point for the original problem. Moreover, the objective function evaluated at $\hat{p}_{int}^*$ is an upper bound on $p_{int}^*$, $$L = \hat{p}_{int}^* \geq p_{int}^* \qquad (26)$$

Therefore, $\hat{x}_{int}^*$ cannot be more than (U–L)-suboptimal for the original problem.

After the problem has been relaxed, the relaxed problem can be expressed as a geometric program, that is, minimizing a posynomial function under posynomial inequality constraints, by means of a change of variable and a transformation of the objective and constraints functions. After the transformation, the problem can be effectively solved using polynomial-time interior-point algorithms.

First, the problem can be restated in terms of minimizing the inverse of the data rate, that is, $R_r^{-1}(N_{h,r}, N_{s,r})$. Then, the new objective function and all the constraints can be expressed in monomial and posynomial form. The objective function, as well as the minimum rate function, is a monomial function, $N_{h,r}^{-1} N_{s,r}^{-1}$. The same holds for the constraint functions defined is (23), and for the SINR function defined in (9).

The SINR constraint in (19) is considered first. Note that in the distributed optimization problem the only variables are the code and the frame length calculated by the receiver, $N_{s,r}$ and $N_{h,r}$. If the following is defined:

$$\alpha_r = P_r g_{r,r} T_c, \qquad (27)$$

$$\beta_k = \frac{\sigma^2 T_c P_k g_{k,r}}{N_{h,k}}, \qquad (28)$$

then (19) can be rewritten as a posynomial constraint $$\eta N_{s,r}^{-1} N_{h,r}^{-1} + N_{s,r}^{-1} \sum_{k \in I_r} \beta_k \leq \frac{\alpha_r}{SINR_{min}}. \qquad (29)$$

For the remaining ($|I_r|-1$) SINR constraints, if we define $$\gamma_i = P_i g_{i,i} T_c N_{h,i} N_{s,i}, \varepsilon_i = \sigma^2 T_c P_r g_{r,i} N_{h,i}, \delta_i = \Sigma_{k \in I_i} \sigma^2 T_c P_k g_{k,i} N_{h,i} / N_{h,k} \qquad (30)$$

then (20) can be rewritten as $$\frac{\eta + \delta_i + \varepsilon_i N_{h,r}^{-1}}{\gamma_i} \leq \frac{1}{SINR_{min}}, \qquad (31)$$

which is a linear, and thus monomial, constraint. In particular, this constraint shows that the frame length variation only leads to an increase or decrease in the level of interference produced. Moreover, the constraint suggests that the optimal frame length is upper bounded by the co-located node that is experiencing the highest level of interference. Based on these observations, the cooperative optimization problem becomes $$\max_{N_{h,r}, N_{s,r}} R_r^{-1}(N_{h,r}, N_{s,r}) \qquad (32)$$

subject to $$R_r^{-1}(N_{h,r}, N_{s,r}) \geq R_{min}^{-1} \qquad (33)$$

$$\eta N_{s,r}^{-1} N_{h,r}^{-1} + N_{s,r}^{-1} \sum_{k \in I_r} \beta_k \leq \frac{\alpha_r}{SINR_{min}}. \qquad (34)$$

$$N_{h,r} \geq \frac{\varepsilon_i}{\gamma_i SINR_{min}^{-1} - \eta - \delta_i}. \qquad (35)$$

Finally, a geometric program can be in general transformed into a convex program through a logarithmic transformation of the optimization variables. If, $$y = [y_1 y_2] = [\log N_{h,r} \log N_{s,r}], \qquad (36)$$

the objective function and the rate constraint function become $$R_r^{-1}(N_{h,r}, N_{s,r}) = N_{h,r} N_{s,r} = e^{y_1} e^{y_2} = e^{a_0^T y}, \qquad (37)$$

where $a_0 = [1 1]$. The constraint function in (34) becomes $$\eta N_{s,r}^{-1} N_{h,r}^{-1} + N_{s,r}^{-1} \Sigma_{k \in I_r} \beta_k = \eta (e^{y_1})^{-1} (e^{y_2})^{-1} + \Sigma_{k \in I_r} \beta_k (e^{y_2})^{-1} = e^{a_1^T y + b_1} + e^{a_2^T y + b_2} \qquad (38)$$

where $a_{-1} = [-1 -1]$, $a_2 = [0 -1]$, $b_1 = \log \eta$ and $b_2 = \log \Sigma_{k \in I_r} \beta_k$. Then, one can transform the problem by taking the logarithm of the objective function and the constraint functions. The resulting problem can be expressed as $$\min_y a_0^T y \qquad (39)$$

subject to $$a_0^T y \leq R_{min}^{-1} \qquad (40)$$

$$\log(e^{a_1^T y + b_1} + e^{a_2^T y + b_2}) \leq \log \frac{\alpha_r}{SINR_{min}} \qquad (41)$$

$$y_1 \geq \log\left(\frac{\varepsilon_i}{\gamma_i SINR_{min}^{-1} - \eta - \delta_i}\right) \qquad (42)$$

$$0 \leq y_1 \leq \log N_{h,max}, y_1 \in \mathbb{R} \qquad (43)$$

$$0 \leq y_2 \leq \log N_{s,max}, y_2 \in \mathbb{R} \qquad (44)$$

$$\forall i \in I_r. \qquad (45)$$

Distributed Energy-minimizing Rate Adaptation. Define:

$E_p$ as the energy per pulse;

$E_b$ as the energy per bit, i.e., $E_b = E_p \cdot N_s$; and $E_s$ as the average energy emitted per second, i.e., $E_s = E_p/(T_c \cdot N_h)$.

The energy per bit is a linear function of the spreading code length, therefore of the number of pulses transmitted per each bit. The average power emitted per second is a function of the inverse of the frame length and hence of the number of pulses transmitted per second. Both depend on the value of $E_p$, which is related to the (electrical) power absorption of the ultrasonic transducer in use.

Modeling the Energy Consumption of a Piezoelectric Transducer. Since electronically driven piezoelectric transducers are known to have minimal current leakage, the majority of power consumption comes from the piezoelectric element. Outside the region of resonance, a piezoelectric ceramic transducer can be viewed (from the electrical point of view) as a parallel plate capacitor with capacitance $C_0$. Thus, the main source of power consumption comes from charging such capacitor. Then, ignoring charge and discharge losses, and considering a capacitor with voltage supply V and pulse repetition frequency f (which corresponds to the charge and discharge frequency of the capacitor), the power consumption $P_c$ can be expressed as $$P_c = f C_0 V^2. \qquad (47)$$

The static capacitance and the voltage supply values can be based on transducer-specific considerations. The static capacitance value of a disc-shaped transducer is given as $$C_0 = \frac{A \varepsilon_0 K}{t_h} [F], \qquad (48)$$

where $\varepsilon_0$ is the permittivity in free air (8.8542 F/m), K is the dielectric constant of the material (adimensional), A [m²] is the area of the disc, and $t_h$ [m] is its thickness. The dielectric constant K depends on material, frequency and mechanical state of the transducer.

Appropriate limits for the voltage supply are derived based on safety concerns, which impose a limit on the radiated acoustic power. No tissue damage occurs in intra-body ultrasonic propagation as long as the acoustic power dissipation in tissues is limited to $10^4$ W/m². From this limit, a corresponding maximum pressure magnitude is derived that can be radiated by the transducer, and consequently the maximum voltage input. For example, if the arm muscle is the primary propagation medium, through the quadratic relation between the acoustic intensity and the acoustic pressure, $I = (P_{RMS})^2/\rho c$, along with known density and speed of sound parameters, the maximum pressure magnitude that can be radiated by the transducer is found to be approximately 0.13 MPa.

The related transducer voltage input can be derived, corresponding to the maximum radiated pressure through the constitutive equation of piezoelectric materials. The latter expresses the relationship among mechanical strain and electrical displacement for the piezoelectric element considering the electrical and mechanical stress and is usually expressed in tensor notation. Here, the so-called converse effect is the material strain proportional to an applied voltage. Assuming a symmetric crystal structure, the constitutive relations reduce to a few parameters. In particular, the so-called $g_{33}$ parameter [Vm/N] represents the piezoelectric voltage coefficient, when the polarization field and the piezoelectrically induced strain are both parallel to the disc axis (usually referred to as the third axis). Based on this, one can express the electric field along the third axis E [V/m] as $E = g_{33} P$, where P again represents the output pressure of the transducer. Since the electric field E can in turn be expressed as the ratio between voltage and electrode distance, we have $V = g_{33} P t_h$. Finally, from (47), the energy consumed to generate a single pulse is obtained as $$E_p = C_0 (g_{33} P t_h)^2 [J]. \qquad (49)$$

Energy-minimizing Rate Adaptation. Based on this model, a rate adaptation strategy is designed where the objective of r is to minimize (i) the energy per bit, $E_b$, or (ii) the average energy emitted per second $E_s$. The problem consists in finding the optimal frame length and the optimal spreading code length that minimize $E_b$ (and/or $E_s$) while meeting the minimum SINR constraints and keeping the data rate over a given threshold. The energy problem is formally expressed below.

$$\min_{N_{h,r}, N_{s,r}} E_b(N_{s,r}) \text{ (or } E_s(N_{h,r})) \text{ subject to (18) (19) (20)}$$

The problem above can also be relaxed to a geometric program as discussed above.

Medium Access Control Protocol. In UsWB, distributed medium access control coordination is achieved by exchanging information on logical control channels, while data packets are transmitted over logical data channels. In one embodiment, unicast transmissions are used between a transmitter TX and a receiver RX. When TX needs to transmit a packet, it first needs to reserve a dedicated channel to RX. The connection is opened through the common control channel, which is implemented through a unique Time Hopping (TH)-sequence and a spreading code known and shared by all network devices.

In the two-way handshake procedure, TX sends a Request-to-Transmit (R2T) packet to RX, which contains its own ID. If RX is idle, a Clear-to-Transmit (C2T) control packet is sent back to TX. In case of failure and, thus, timer expiration, TX will attempt a new transmission after a random backoff time, for a maximum of $N_R$ times. During these initial steps, since an estimate of the current interference level is not available, the transmitter transmits at the minimum data rate, conservatively using a maximum frame length and spreading code length, thus generating low interference. After receiving the C2T, the transmitter switches to a dedicated channel by computing its own TH sequence and spreading code obtained by seeding a pseudo-random sequence generator with its ID. As a consequence, both TX and RX leave the common channel and switch to a dedicated channel. Once the connection has been established, TX sends the first packet using maximum frame and spreading code length. The receiver RX computes the optimal frame and spreading code lengths as discussed above. This information is piggybacked into ACK or NACK packets.

In the explicitly cooperative case, once the communication has been established, RX does not leave the common control channel. Instead, it keeps "listening" to both the dedicated and common control channel at the same time. In the dedicated control channel, RX sends to TX the optimal frame and code lengths to be used for the next transmission. In the common control channel, RX exchanges with other co-located receivers information on the level of tolerable interference.

Performance Evaluation

Performance evaluations of the UsWB embodiment was performed using a custom-designed multi-scale simulator that considers UsWB performance at three different levels, i.e., (i) at the acoustic wave level by modeling ultrasonic propagation in tissues through reflectors and scatterers, (ii) at the bit level by simulating in detail the ultrasonic transmission scheme, (iii) at the packet level by simulating networked operations and distributed medium access control and adaptation.

Figure 10:
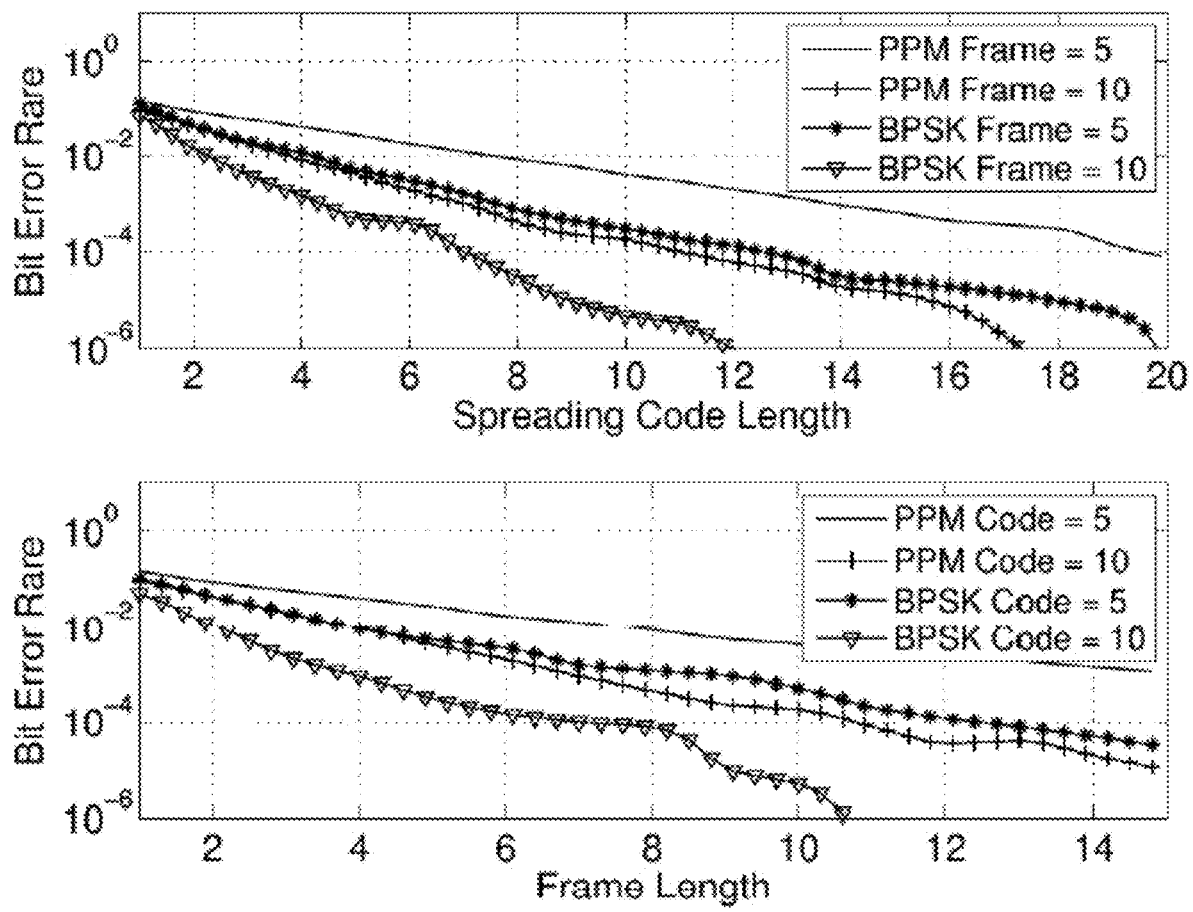
FIG. 10 shows two charts, the first showing BER vs. spreading code length, and the second showing BER vs. TH frame length for PPM-BPSK spread and PPM-PPM spread according to one embodiment of the present invention.

The acoustic wave level simulation is performed as described above. A channel impulse response is obtained by simulating propagation in the human arm. Transmission at the bit level is modeled through a custom physical layer simulator of UsWB, which allows to obtain an empirical model of the Bit Error Rate (BER) against different values of the TH frame length and spreading code length, for different levels of interference. The physical layer simulation models a transmitter and a receiver (located 20 cm apart) communicating over an ultrasonic channel using the UsWB transmission scheme. Each sender node transmits information as discussed above. Simulations are performed to obtain an estimate of the achievable BER upon varying the frame length and the spreading code length with a different number of interferers transmitting on the same channel. Both PPM-BPSK-spread with coherent receiver and the PPM-PPM-spread with non-coherent receiver were implemented. An extensive simulation campaign was conducted and BER values were obtained as a function of the spreading code and frame lengths for different number of simultaneously active connections. FIG. 10 reports the BER values when 4 pairs of nodes are transmitting at the same time, and as expected the coherent PPM-BPSK-spread outperforms the non-coherent PPM-PPM-spread. The empirical model of the BER as a function of frame length and spreading code length for a given level of interference is then imported in a Java-based event-driven packet-level simulator, which models all aspects of the UsWB communication protocol stack.

Figure 11:
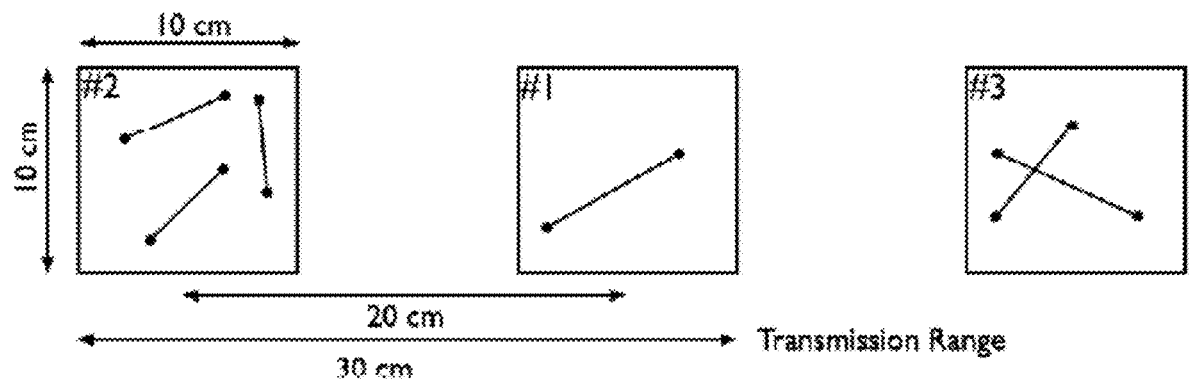
FIG. 11 is a set of images showing network simulation topology according to one embodiment of the present invention.

Network Simulation Topology. Two different settings were considered for the network level simulations. First, a 2-D topology was considered with 18 static nodes randomly located inside a square of side 20 cm. A maximum of nine communicating pairs are considered. We also assume that the transmission range is greater than the maximum distance between the nodes. Thus all nodes measure the same number of interferers. The second setting consists of three 2-D squared clusters of nodes with side 10 cm, displaced 20 cm apart from each other (distance center-to-center). In each cluster, the nodes are randomly deployed according to a gaussian distribution. The cluster (#1) in the middle contains one communicating pair, while the other clusters, (#2) and (#3), contain a variable number of communicating pairs. The transmission range is assumed to be of 30 cm. Thus, all the nodes of adjacent clusters interfere with each other, while nodes of non-adjacent clusters do not. Under this assumption, communicating pairs from different clusters measure different levels of interference. The second scenario topology is shown in FIG. 11.

During the simulations, the frame length and spreading code length are adapted to the interference level measured at the receiver according to one of the objectives discussed above. In particular, the first setting matches the condition required by the implicitly cooperative problem in (30), while for the second setting the explicitly cooperative problem in (17) is considered. The simulation time is set to 100 s and nodes start establishing connections at a random time instant but no later than 2 s after the simulation start time. An infinite arrival rate at each transmitter is considered, i.e., transmitters are always backlogged. The maximum allowed frame and spreading code length is set to 15 slots and 20 chips, respectively. The maximum supported rate, achieved when frame and spreading code length are both set to one, is equal to 2 Mbit/s. The minimum SINR constraint leads to a maximum BER constraint of $10^{-6}$.

Performance is first analyzed (in terms of throughput and packet drop rate) of the rate-maximizing solution coming from both the implicit and explicit cooperative problems. Throughput is defined as the average rate of information correctly received during the simulation time per active connection. The packet drop rate is defined as the ratio between the number of packets dropped and the number of packets generated at the application layer, averaged over all the active connections. Both performance metrics are evaluated as a function of the number of active connections N.

Figure 12:
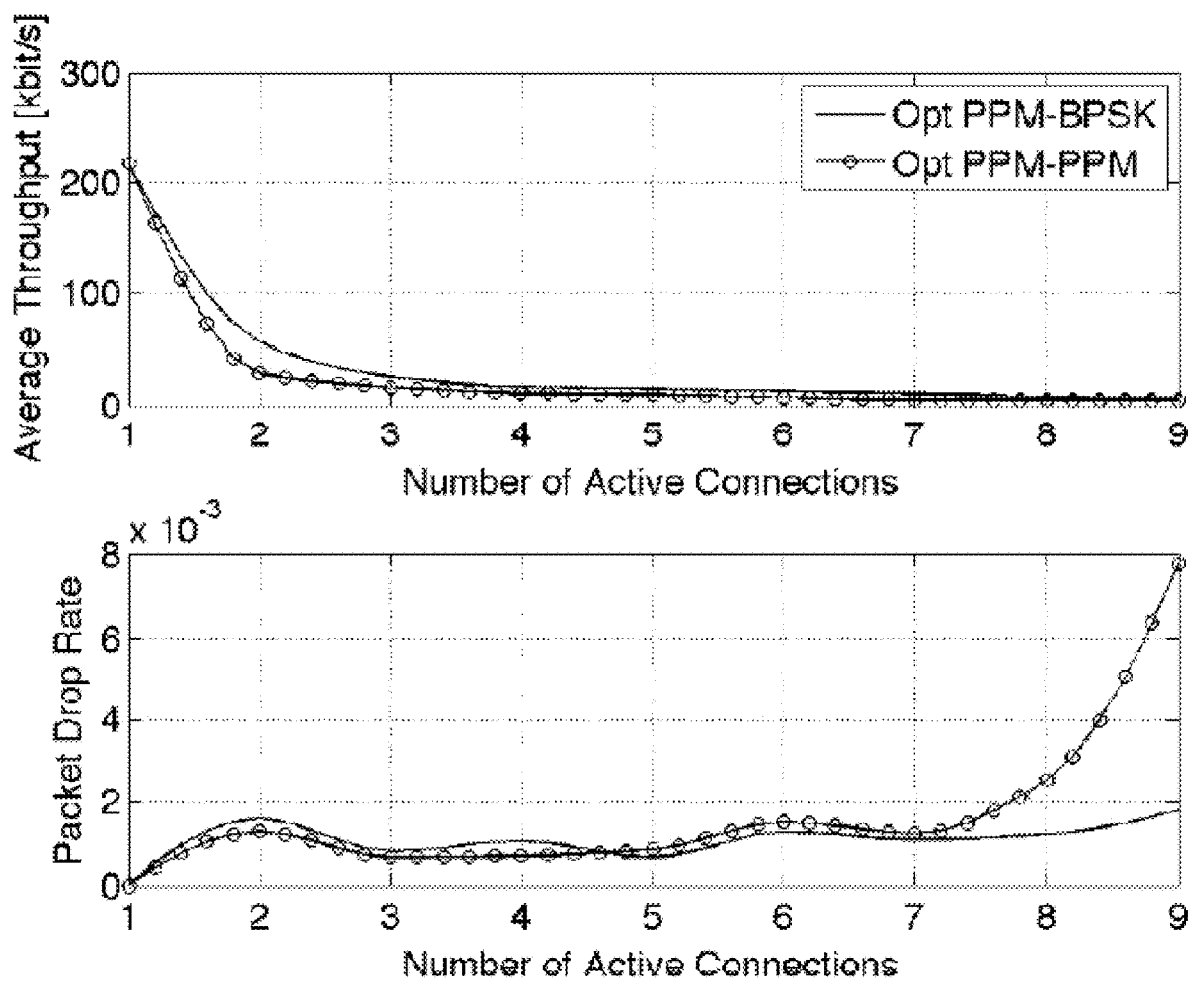
FIG. 12 is a set of graphs showing average throughput [kbits/s] and packet drop rate with rate-maximizing solutions for the implicitly cooperative problem according to one embodiment of the present invention.

Rate Maximization—Implicitly cooperative solution. In FIG. 12 network throughput and packet drop rate for the rate-maximizing strategy are compared, when frame and code length are adaptively regulated based on the implicitly cooperative problem. The rate-maximizing solution is presented for both the transmission schemes discussed above, i.e., the PPM-BPSK-spread with coherent receiver and the PPM-PPM-spread with non-coherent receiver. As expected the coherent PPM-BPSK solution performs better in terms of throughput. This happens because the BER constraint is satisfied for lower values of frame length and code length, which leads to higher data rates according to (7). When the number of active connections is equal to one, i.e., there are no interferers, both systems achieve the same throughput since the same optimal pair is used, (2,2).

In terms of packet drop rate, for the coherent PPM-BPSK system the BER constraint is satisfied for any number of active connections considered. Instead, for the non-coherent PPM-PPM system, when the number of active connections is greater than 7, the BER constraint cannot be satisfied anymore, and therefore the packet drop rate increases. Note that this problem can be overcome by simply relaxing the constraint on the maximum size of code length or frame length, without relaxing the constraint on the maximum BER. This may lead to a lower data rate.

Figure 13:
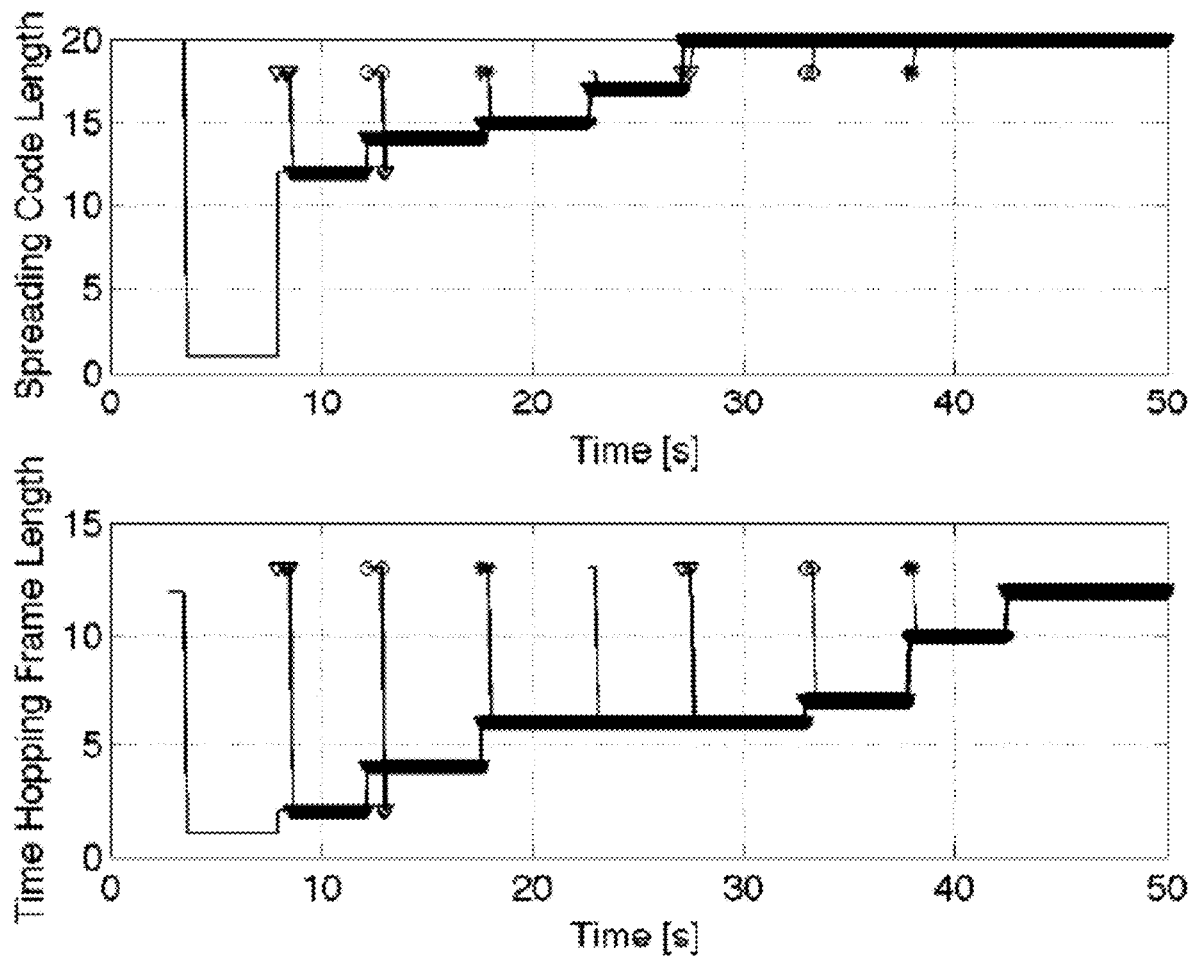
FIG. 13 is a set of graphs showing time evolution of spreading code length $N_s$ (top) and time-hopping frame length $N_h$ (bottom) for the implicitly cooperative problem according to one embodiment of the present invention.

The dynamic adaptation of the frame and code length performed distributively by each node is analyzed. Focusing on the coherent system, in FIG. 13 shows the evolution in time of frame and code length when 9 different connections are asynchronously activated with a deterministic 5 s delay between each other. Each connection starts with the maximum supported frame and code length and then adaptively reaches the optimal value based on the interference level measured at the receiver. Since the number of interferers is the same for each receiver, the locally optimal solution is also globally optimal.

Figure 14:
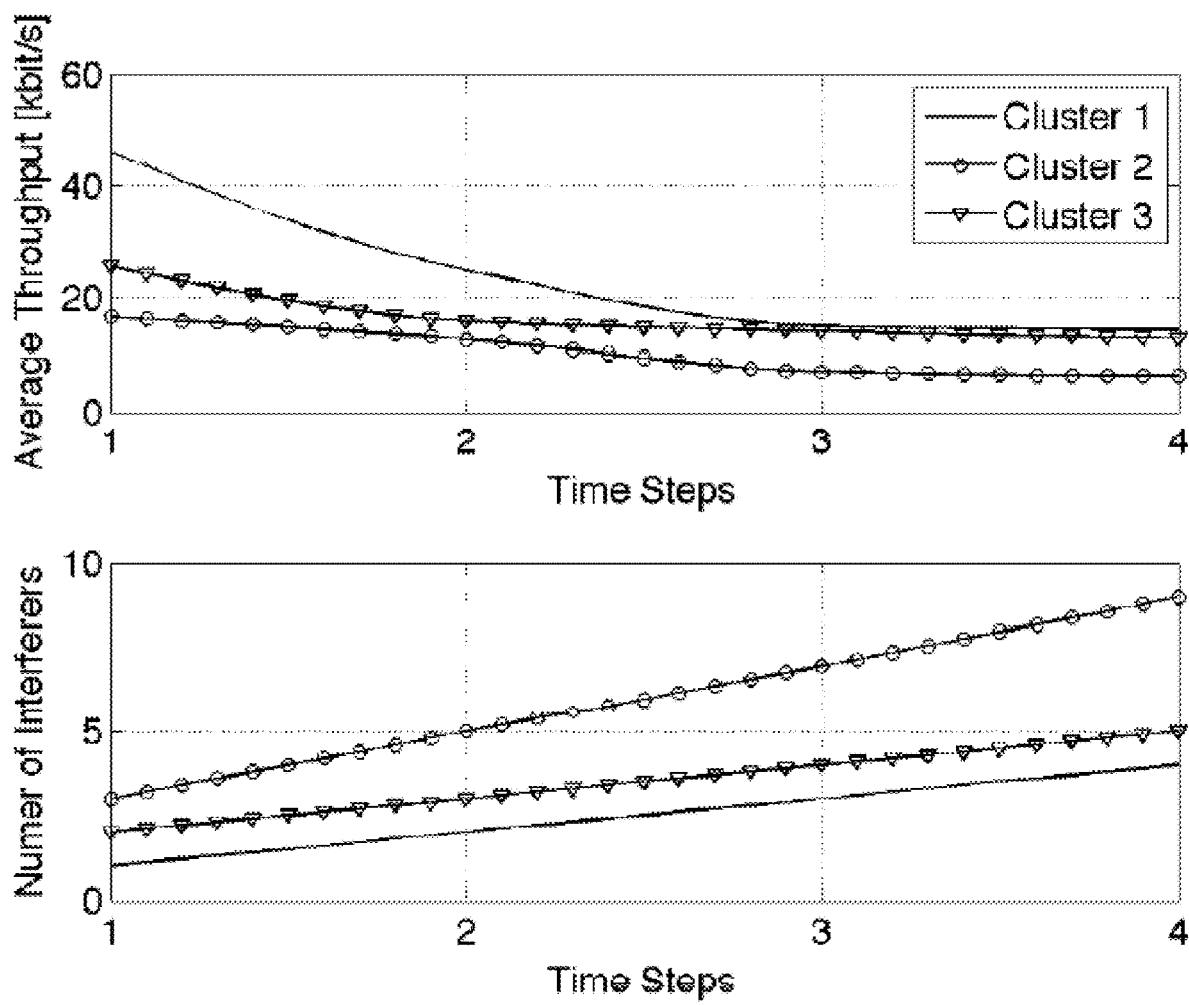
FIG. 14 is a set of graphs showing average throughput [kbit/s] and number of interferers for the explicitly cooperative problem for different time steps according to one embodiment of the present invention.
Figure 15:
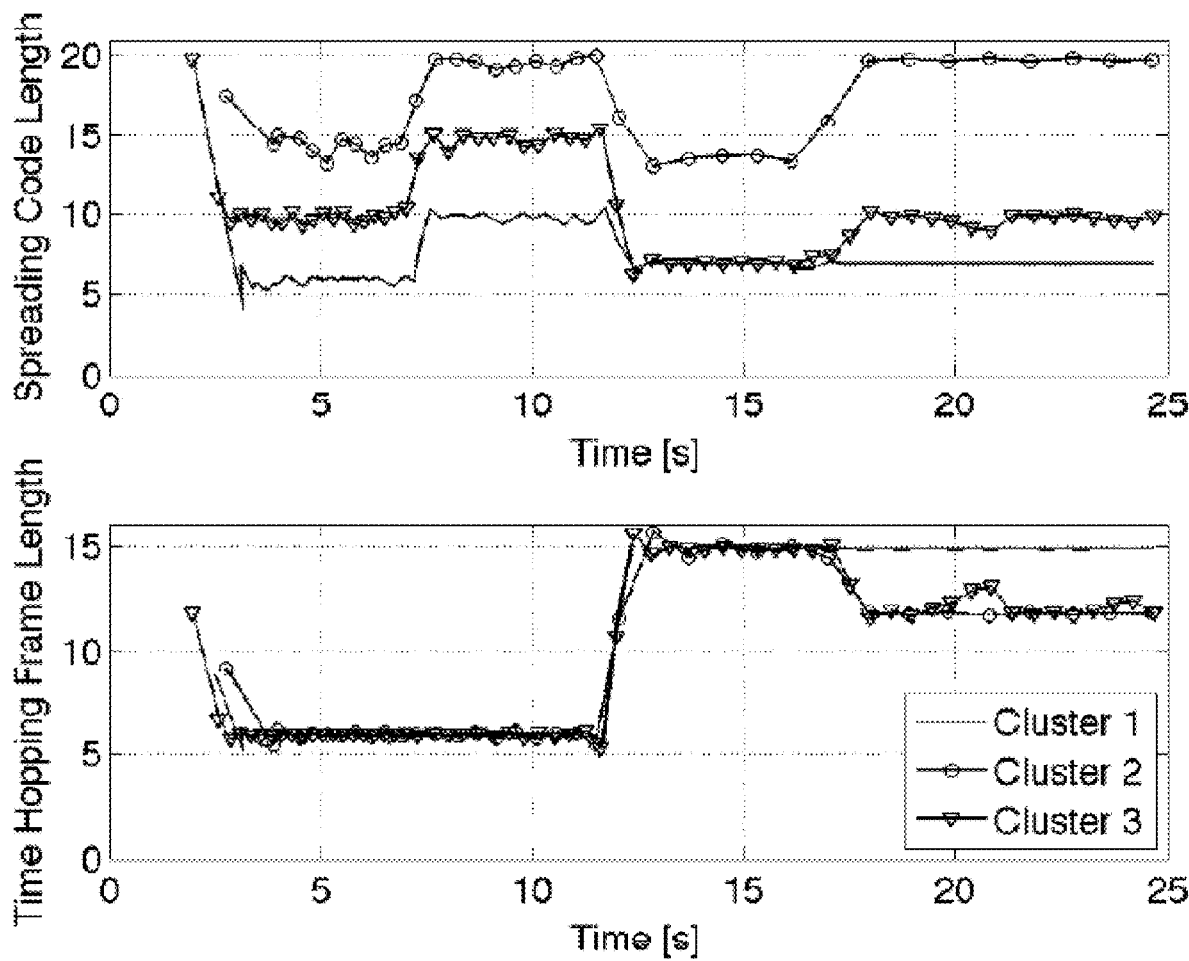
FIG. 15 is a set of graphs showing time evolution of spreading code and TH frame lengths for the explicitly cooperative problem according to one embodiment of the present invention.

Explicitly cooperative solution. In FIG. 14 the network throughput is plotted when frame and code length are adaptively regulated based on the explicitly cooperative problem in (17). The solution is presented for the PPM-BPSK-spread transmission strategies. Throughput is evaluated by varying the number of active connections in four consecutive time steps. In particular, it is assumed that there is always one active connection in cluster #2. Cluster #1 and #3, activate a new connection at each time step. In FIG. 14, the average number of interferers is reported, measured by the receivers in each cluster. The cluster located in the middle, hence located within the transmission range of both the other two clusters, measures a higher level of interference, and therefore achieves a lower throughput. However, since the BER constraint is satisfied by all nodes in the three clusters, a low packet drop rate is achieved. Finally, in FIG. 15 the dynamic behavior of the frame and code length adaptation is shown. Consider two new connections activated asynchronously every 5 s in Cluster #1 and #3. In each cluster, the frame and code length are adapted according to the increasing level of interference measured in the channel. In particular, the effect of the constraint in (35), which forces the frame length to be greater than or equal to the frame length of the connection that is experiencing the highest level of interference, i.e., the connection in Cluster #2.

Figure 16:
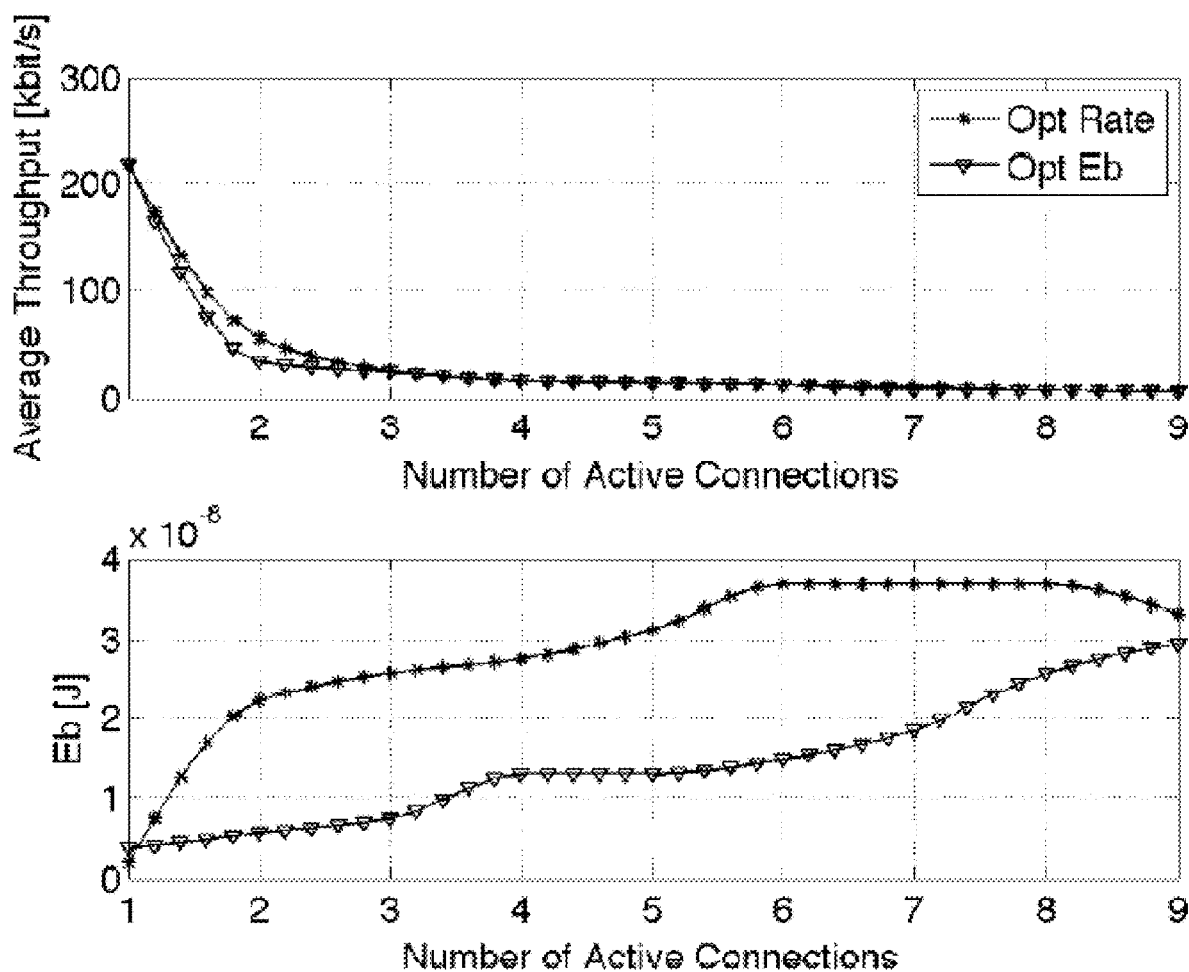
FIG. 16 is a set of graphs showing throughput and $E_b$ vs. the number of active connections for rate maximizing and energy minimization strategies according to one embodiment of the present invention.

Rate-optimal Vs. Energy-optimal Results. In FIG. 16 the throughput obtained by adapting the transmission rate according to an energy-minimizing strategy is shown. The energy-minimizing strategy is also compared to the rate-maximizing strategy introduced in terms of data rate and energy consumption. The throughput achievable in case of the rate-maximizing solution is comparable to what is obtained with the energy-optimized solution. When the number of active connections, N, is lower than 2, the throughput of the $E_b$-optimal strategy is close to the throughput of the rate-maximizing scheme. For N higher than 2, the two considered strategies show a similar throughput performance. Since the maximum BER constraint is always satisfied, the rate-maximizing and the energy-minimizing strategies lead to packet drop rates close to zero. Finally, the energy consumption obtained with the $E_b$-optimal solution, is always better that what can be obtained using the rate-maximizing scheme. This result assumes that each node transmits at the maximum power allowed that gives a value of energy per pulse of $E_p$=1.8436 nJ obtained using the model presented above with parameters reported in Table IV.

TABLE IV

Parameters for the Disc-Shaped Piezoelectric Element

| A [mm$^2$] | $t_h$ [mm] | K | $g_{33}$ [N/m] |
|---|---|---|---|
| 0.201 | 0.47 | 1800 | 0.027 |

UsWB FPGA Prototype

A software-defined testbed architecture for ultrasonic intra-body area networks was created to demonstrate the feasibility of ultrasonic communications in biological tissues. The UsWB embodiment was implemented in an FPGA-based prototype. As shown below, the prototype can flexibly trade off performance for power consumption, and achieve, for bit error rates (BER) no higher than $10^{-6}$, either (i) high-data rate transmissions up to 700 kbit/s at a transmit power of 22 dBm ($\approx$158 mW), or (ii) low-data rate and ultra-low-power transmissions down to −17 dBm ($\approx$19 µW) at 9 kbit/s (in addition to numerous intermediate configurations). The UsWB MAC protocol allows multiple transmitter-receiver pairs to coexist and dynamically adapt the transmission rate according to channel and interference conditions to maximize throughput while satisfying pre-defined reliability constraints. Finally, a statistical model of small-scale fading for the ultrasonic intra-body channel is disclosed.

Figure 17:
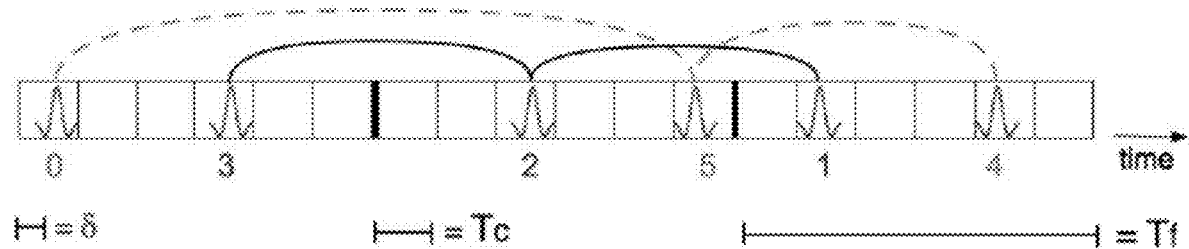
FIG. 17 is a graph showing two concurrent transmissions with Nh=6, Ns=3, time-hopping sequences {3,2,1} and {0,5,4} and spreading codes {1,1,-1} and {1,-1,-1} according to one embodiment of the present invention.

Prototype Physical Layer. Consider, as in FIG. 17, a slotted timeline divided in slots of duration $T_c$, with slots organized in frames of duration $T_f=N_hT_c$, where $N_h$ is the number of slots per frame. Each user transmits one pulse per frame in a slot determined by a pseudo-random time-hopping sequence. Information is carried through pulse position modulation (PPM), i.e., a '1' symbol is carried by a pulse delayed by a time δ with respect to the beginning of the slot, while a '−1' symbol begins with the slot. Since a single pulse may collide with pulses transmitted by other users with a probability that depends on the frame size $N_h$, we represent each information bit with pseudo-orthogonal spreading codes of variable length, $N_s$ because of (i) their multiple access performance, (ii) limited computational complexity, and (iii) inherent resilience to multipath. The resulting transmitted signal for a symbol d can be modeled as $$s(t) = \sum_{j=0}^{N_s-1} p\left(t - c_j T_c - jT_f - \frac{a_j d + 1}{2}\delta\right)$$

where p(t) is the pulse shape, $\{c_j\}$ is the time-hopping sequence with $0 \leq c_j \leq N_h-1$, $\{a_j\}$ is the pseudo-orthogonal spreading code of $N_s$ chips with $a_j \in \{-1, 1\}$, and δ is the PPM shift of a pulse representing a '1' chip.

Prototype Medium Access Control. The low-duty-cycle impulse-based transmission scheme with a superimposed spreading code allows multiple transmitters to coexist on the same channel. In UsWB, by dynamically and distributively adapting their time-hopping frame length and spreading code length, multiple users coexist without the need for mutual temporal exclusion between different transmissions (which is hard to achieve in ultrasonic channels affected by long propagation delays). By adapting frame and code length, users control the tradeoffs among (i) resilience to multi-user interference and ultrasonic channel errors, (ii) achievable information rate, and (iii) energy efficiency. By controlling the time-hopping frame length $N_h$, i.e., the average inter-pulse time, a user can adapt the transmission rate (which decreases with larger time-hopping frame), and as a consequence modify the average radiated power and therefore the level of interference generated to other ongoing communications. By controlling $N_s$, i.e., the number of pulses per information bit, a user can control the tradeoff between robustness to multi-user interference and noise (which increases with longer spreading codes), energy consumption per bit (which increases linearly with increasing $N_s$) and information rate (decreasing with increasing $N_s$). UsWB optimally, distributively, and asynchronously regulates these tradeoffs to (i) maximize the communication rate, or (ii) minimize the energy consumption.

Each user distributively maximizes its transmission rate by selecting an optimal pair of code and frame lengths based on the current level of interference and channel quality for a given maximum tolerable BER. Rate adaptation is achieved through an ad-hoc designed protocol. A two-way handshake opens the connection between two nodes, $T_x$ and $R_x$. $T_x$ sends a Request-to-Transmit (R2T) packet to $R_x$. If $R_x$ is idle, a Clear-to-Transmit (C2T) packet is sent back to $T_x$. Once the connection has been established, the receiver $R_x$ estimates the interference and calculates the frame and spreading code lengths that maximize the communication throughput. This information is piggybacked into ACK or NACK packets.

UsWB Prototype Ultrasonic Testbed Architecture

Figure 18:
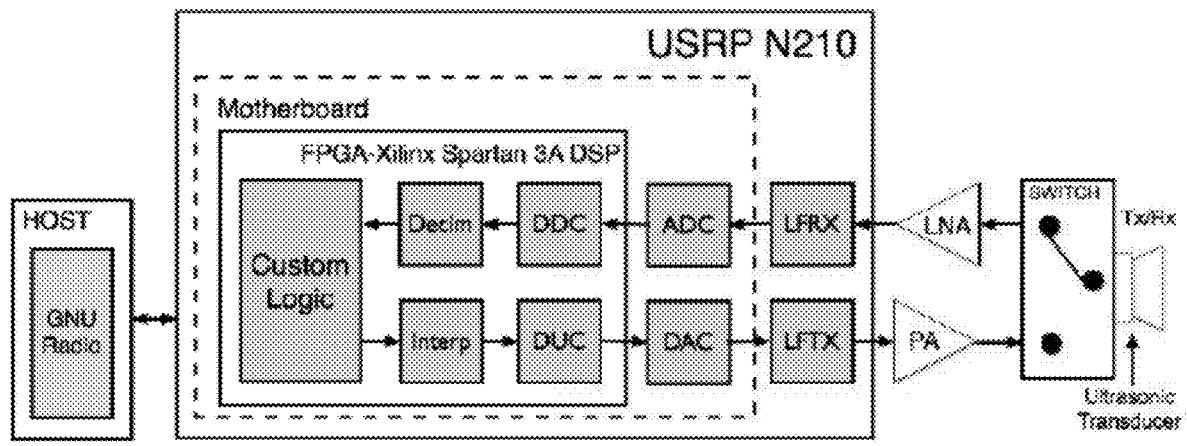
FIG. 18 is a diagram of a hardware architecture of an ultrasonic software-defined node according to one embodiment of the present invention.

A reconfigurable platform was designed to test ultrasonic communication and networking schemes. The testbed consists of ultrasonic software-defined nodes communicating through ultrasonic phantoms that emulate acoustic propagation through biological tissues with high fidelity. The proposed hardware architecture of an ultrasonic software defined node is illustrated in FIG. 18. It comprises (i) a Universal Software Radio Peripheral (USRP) N210, (ii) a host machine, (iii) an electronic switch, (iv) an amplification stage, (v) and a high-frequency ultrasonic transducer.

USRP N210. Several Software Defined Radio (SDR) development platforms are available where Field-Programmable Gate Arrays (FPGAs) or specialized processors are used for high-sample-rate digital signal processing. Among these, USRP was used because of its low cost and wide adoption in academia and industry. USRP N210 consists of a motherboard and two daughterboards. The motherboard is the main processing unit, and incorporates AD/DA converters (a dual 100 MSPS 14-bit ADC and a dual 400 MSPS 16-bit DAC), and an FPGA unit (Spartan 3A-DSP 3400). The daughterboards are RF front-ends that interface the device with transmitter or receiver antennas. LFTX and LFRX daughterboards were used, that operate from DC to 30 MHz, which includes ultrasonic frequency ranges of interest.

In USRP, the system complexity is shifted from hardware to software and most of the computational load is typically left to the host machine. However, the host machine can become the computational bottleneck of the communication system, while the connection between host and USRP introduces delays preventing accurate timing of network protocols. As discussed in detail in what follows, this problem is overcome by shifting (with respect to the typical GNU Radio/USRP architecture) significant components of the signal processing on the on-board FPGA.

Host Machine. The host machine can be either a desktop/laptop computer or a computer-on-module, e.g., Gumstix, connected to the USRP through a Gigabit Ethernet (GbE) link. In the traditional GNU Radio/USRP architecture, the host machine runs all the software-defined signal processing functionalities implemented with the GNU Radio development toolkit. However, most PHY and MAC functionalities were implemented in the FPGA embedded in the USRP. Therefore, in the prototype design the host machine only configures and initializes the USRP, and generates/receives application-layer bit streams.

Electronic Switch. To reduce the testbed complexity and cost, an electronic switch is used that allows a single ultrasonic transducer to transmit and receive on a time division basis. The switching operation is piloted both from the host machine and the USRP FPGA by connecting the switch with the General Purpose Input/Output (GPIO) digital pins available on the LFTX and LFRX daughterboards. A commercial off-the-shelf (COTS) switch, Mini-Circuits ZX80-DR230+, that comes in a connectorized package with embedded coaxial RF connectors, and offers low insertion loss and very high isolation over the entire frequency range (0-3 GHz).

Amplification Stage. An external amplification stage was produced. The low-power output of the LFTX daughterboards, about 3 dBm 2 mW), can limit the maximum transmission range supported. Therefore, at the transmitter a connectorized COTS Power Amplifier (PA), Mini-Circuits ZPUL-30P, was used specifically designed for short-pulse transmissions with a maximum output power of 22 dBm. In the receiver chain, LFRX daughterboards have almost no gain. Thus, a connectorized COTS Low-Noise Amplifier (LNA), Mini-Circuits ZFL-1000LN+, was used with a noise figure of 2.9 dB.

Ultrasonic Transducers. An ultrasonic transducer is a device capable of transmitting and receiving ultrasonic waves. Most commercial ultrasonic transducers are based on the piezoelectric effect, which allows converting electrical energy in ultrasonic energy, and vice versa. To communicate in human tissues over a range of several centimeters transducers operating at frequencies in the order of a few MHz are needed. Moreover, high-bandwidth transducers are necessary to implement wideband transmission schemes such as UsWB. The only COTS ultrasonic transducers that nearly match these requirements are those designed for nondestructive analysis applications, since high frequencies and large bandwidth are required for fine material characterization. However, these transducers are not optimized in terms of coupling electromechanical efficiency, and thus introduce significant energy conversion losses. In the prototype, standard immersion W-series ultrasonic transducers, Ultran WS37-5, were used. The nominal bandwidth central frequency is about 5 MHz and the bandwidth at −6 dB goes from 50% to 100% of the bandwidth central frequency, i.e., 2.5-5 MHz.

Ultrasonic Phantoms. Ultrasonic phantoms are used to emulate the intra-body ultrasonic communication channel with high fidelity. Commonly employed in medical ultrasound research, ultrasonic phantoms are composed of soft and hard tissue-mimicking materials, also known as tissue substitutes. These materials have the same acoustic propagation properties of human tissues, e.g., sound speed, density, and attenuation. Off-the-shelf ultrasonic phantoms that emulate the interactions between ultrasounds and the human body, tissues, organs and systems are available.

A human-kidney phantom was immersed in a background water-based gel, whose acoustic characteristics are reported in Table V. The background gel is almost lossless, and has the same density and sound speed as the kidney. Therefore, reflections and refractions are minimum between the kidney and the gel. Thus, the latter can be considered acoustically transparent. The phantom dimensions are approximately 10×16×20 cm.

TABLE V

Ultrasonic Phantom Acoustic Characteristics

| Tissue | Speed, v | Attenuation, $\alpha$ | Density, $\rho$ |
| --- | --- | --- | --- |
| Background Gel | 1550 m/s | <0.1 dB/cm | 1020 Kg/m$^3$ |
| Kidney | 1550 m/s | 2 dB/cm @ 5 MHz | 1030 Kg/m$^3$ |

Architecture of the Prototype Communication System

Signal processing, algorithms and protocols can be implemented in the ultrasonic software-defined node using a framework that combines (i) the GNU Radio software development toolkit and (ii) the open source Hardware Description Language (HDL) design for the FPGA embedded in the USRP. In GNU Radio, most of the digital signal processing is performed on the external host. When using HDL design most signal processing operations are moved to the embedded FPGA. Tradeoffs between these two different approaches are discussed.

GNU Radio Vs. HDL PHY Layer Implementation. Wideband pulse-based communications can significantly mitigate the multipath effect caused by the heterogeneity of the human body. However, shorter pulses have wider bandwidth, which results in higher sampling rates that can overload the host machine or the Gigabit Ethernet (GbE) link between the host machine and the USRP. In an initial design, UsWB PHY layer functionalities were implemented on the host machine using GNU Radio. However, (i) the capacity of the GbE link between the host machine and the USRP limits the maximum achievable sample rate, i.e., 25 million samples per second, thus the maximum achievable signal bandwidth. When exceeding the link capacity, Ethernet frames coming from/to the USRP are dropped at the network interfaces, with consequent loss of the carried digital samples; (ii) digital signal processing operations implemented in GNU Radio, e.g., digital filters, overload the host machine when operating at high sampling rates, i.e., greater than 10 million samples per second. If the host machine is unable to process data fast enough, the internal buffers that store digital samples overflow, thus causing loss of large amount of digital samples.

It became apparent that the above limitations would prevent successful implementation of UsWB in GNU Radio. For these reasons, all PHY layer functionalities were implemented in the embedded FPGA. This effectively speeds up data processing and reduces the computational load on the host machine.

Partial Reconfiguration. In exchange for these benefits comes lower system flexibility. The HDL design needs to be synthesized before it can be loaded in the embedded FPGA. Thus, changing the PHY layer structure and parameters at runtime is not as simple as doing it in GNU Radio on the host machine. Still, the HDL modules can be designed such that partial PHY layer reconfiguration is achievable at runtime through a group of setting registers implemented on the FPGA that can be accessed by the host machine. Through these setting registers, one can reconfigure key parameters of the PHY layer transmission scheme (i.e., pulse shape and code length, among others) or even select which PHY blocks should be used, thus modifying at runtime the structure of the PHY layer chain.

MAC Layer Design Challenges. Similarly, MAC-layer functionalities can potentially be implemented in the host machine or in the embedded FPGA. Highly customized or reconfigurable and complex protocols can be challenging to implement on FPGA and likely cause overutilization of the available FPGA hardware resources. An alternative is then to implement the MAC layer on the host machine, by using high-level languages and libraries available in GNU Radio. However, MAC protocols require highly precise packet timing and small, precise interframe spacings in the order of microseconds. GbE link and the GNU Radio processing latency are in the order of milliseconds. Hence, time-critical radio or MAC functions cannot be placed in the host machine.

In the current system architecture the MAC layer is implemented in HDL, and the FPGA setting registers enable partial reconfiguration at runtime. An implementation of a hybrid solution is possible based on a softcore processor implemented in the embedded FPGA.

Prototype Tx and Rx HDL Architecture

The default USRP HDL design operates on digital waveforms coming from and going to the host machine and performs only digital down and up conversion (DDC/DUC), decimation and interpolation. PHY and MAC layer digital processing takes place on the host machine. A different approach was taken, as the USRP HDL code was customized and extended to implement UsWB PHY and MAC layer operations in the FPGA.

Figure 19:
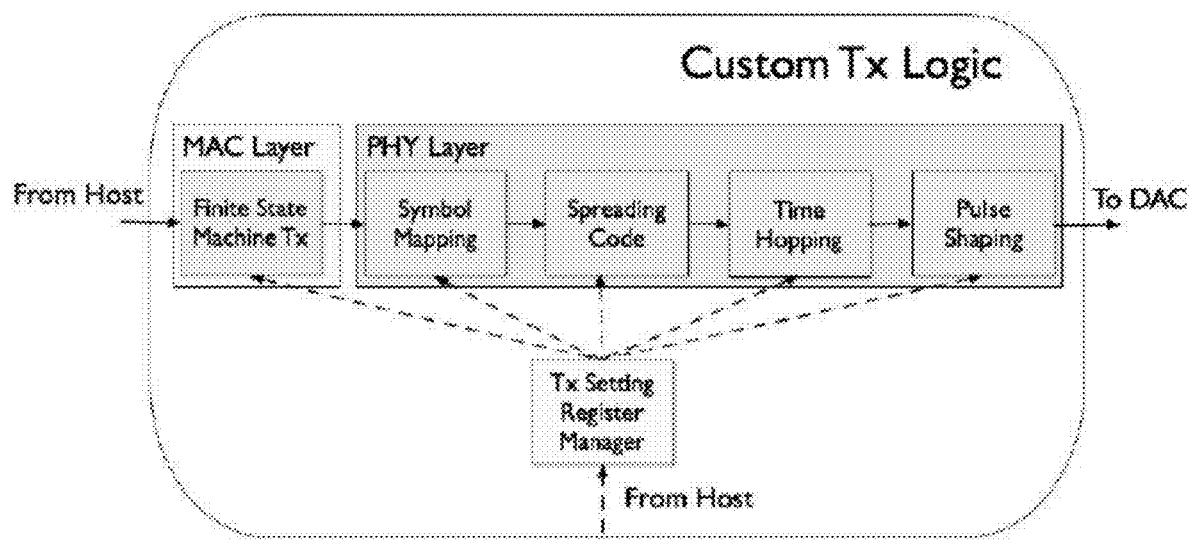
FIG. 19 is a block logic diagram of a custom transmitter according to one embodiment of the present invention.

Custom Transmitter Chain. FIG. 19 shows a block diagram of the custom transmitter logic. Since PHY and MAC functionalities are implemented on the FPGA, input data are raw information bits that need to be packetized and encoded in digital waveforms. After MAC and PHY layer operations, the custom transmitter logic outputs the digital quantized signal to be transmitted. This is then digital-to-analog converted, amplified and finally converted into an ultrasonic signal by the transmitter transducer.

Transmitter MAC Finite State Machine. Raw information bits from the host are received at the transmitter MAC-layer Finite State Machine (FSM-Tx), which implements UsWB MAC functionalities (including packetization) and coordinates the PHY layer operations implemented by the other blocks of the chain. The UsWB MAC-layer data structure, i.e., UsWB packet is created in the FSM-Tx. The word "packet" is intentionally used instead of "frame" to avoid confusion with the time-hopping frame. The UsWB packet starts after a Packet Synchronization Preamble (PSP) and a Time-Hopping Synchronization Preamble (THSP). The former enables coarse synchronization that allows the receiver to detect an incoming packet, while the latter allows identifying the exact start time of the time-hopping frame. The UsWB packet is then serialized, i.e., converted into a sequence of bits, and forwarded to the next module in the chain, i.e., Symbol Mapping. The FSM-Tx also controls the time-hopping frame length $N_h$ and spreading code length $N_s$ used by the PHY layer, according to feedback information from the receiver.

Transmitter PHY Layer. The first block of the transmitter PHY layer chain is Symbol Mapping. Here, raw information bits are mapped into $\{-1,1\}$ binary symbols. The binary symbols are then spread in chips by the Spreading Code module following a pseudo-random spreading code. For each symbol, this block outputs $N_s$ chips in $\{-1,1\}$. Chips are then forwarded to the Time-Hopping module that spreads them in time according to the selected time-hopping pattern. The output of this block is a sequence of $\{-1,1\}$ chips, one per time-hopping frame. Finally, the Pulse Shaping module maps the incoming chips to position-modulated pulses. The output is a train of position-modulated pulses following a predefined time-hopping pattern.

Figure 20A:
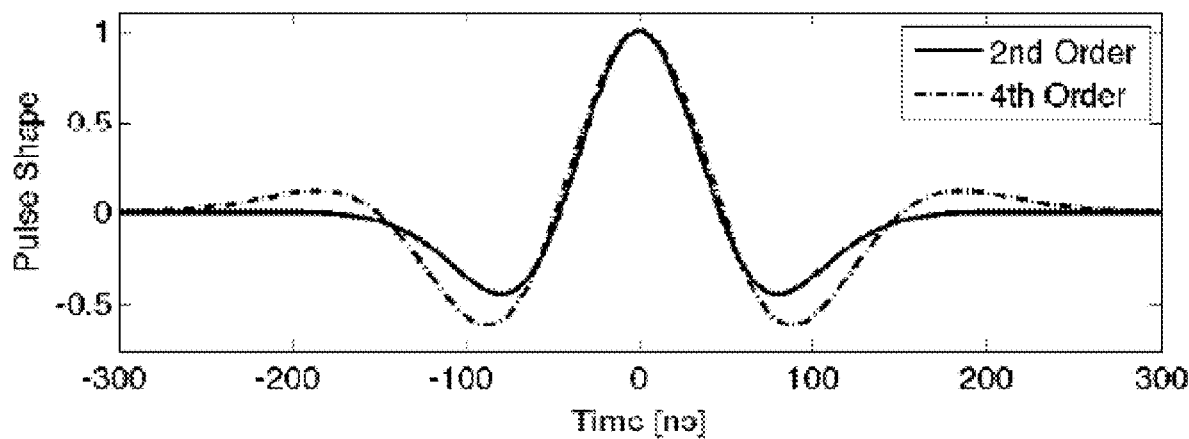
FIG. 20a is a graph showing $2^{nd}$ order and $4^{th}$ order derivative gaussian pulses according to one embodiment of the present invention.
Figure 20B:
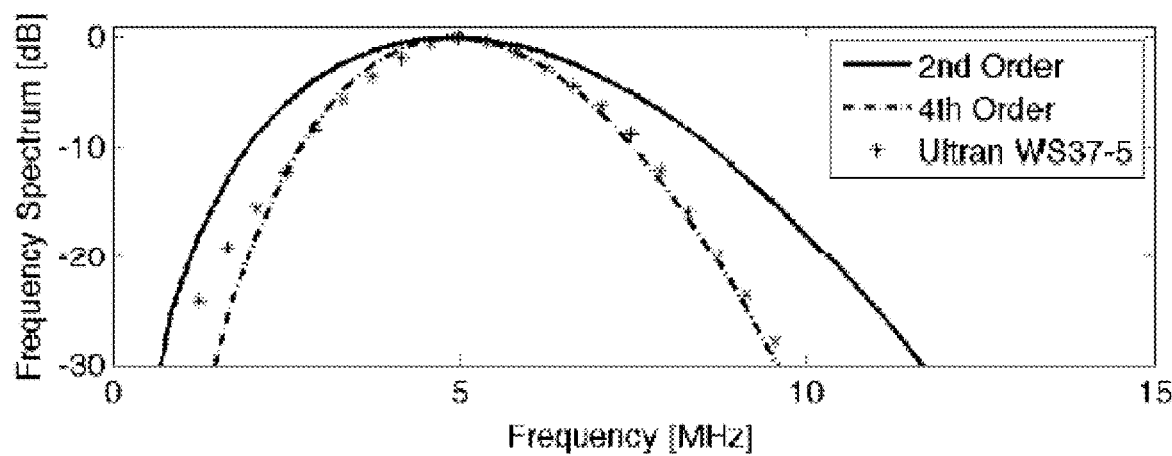
FIG. 20b is a graph showing $2^{nd}$ order and $4^{th}$ order derivative gaussian pulses compared in frequency domain with the Ultran WS37-5 frequency response according to one embodiment of the present invention.

Pulse Shaping. The Pulse Shaping module consists of a Finite Impulse Response (FIR) filter whose coefficients, i.e., taps, represent the samples of a 4th-order derivative gaussian pulse. The original design discussed was based on a 2nd-order derivative gaussian pulse. However, to match the central frequency and bandwidth requirements of the ultrasonic transducers in use, a higher-order derivative gaussian pulse was adopted, characterized by higher central frequency and lower relative bandwidth. In FIG. 20a and FIG. 20b the two pulse shapes are compared in the time and frequency domains. FIG. 20b also shows a 4th-order derivative pulse shaped to match the frequency response of the Ultran WS37-5 ultrasonic transducer. The pulse duration is approximately 300 ns, with a PPM shift of 60 ns, within a time-hopping slot ($T_c$) of 360 ns. The resulting maximum raw chip rate is 2.78 Mchip/s, which results in a maximum raw data rate of 2.78 Mbit/s when time-hopping frame and spreading code lengths are both set to 1.

Transmitter Setting Register Manager. The Transmitter Setting Register Manager (SRM-Tx) is in charge of routing configuration parameters written by the host machine into the setting registers. Whenever the host machine updates any of the setting registers, the SRM-Tx is triggered to read the register content and route it to the destination module. This block enables real-time reconfiguration thus enhancing the transmitter flexibility. The communication system is designed to allow real-time reconfiguration of several parameters, i.e., spreading code and spreading code length, time-hopping frame length and timehopping sequence, packet payload size, SPD sequence and SPD length, and length of the preambles. One can also change the pulse shape in real time through FIR filters with reloadable taps.

Moreover, by carefully rerouting the binary flow, registers can be used to enable and disable selected modules to reconfigure in real time the entire chain structure, thus modifying the communication system architecture. For example, adaptive modulation can be implemented by switching between different Symbol Mapping modules at runtime to change the symbol constellation used. Moreover, the Time-Hopping module or the Spreading Code module can be disabled to obtain pure spreading-code or time-hopping based schemes.

Figure 21:
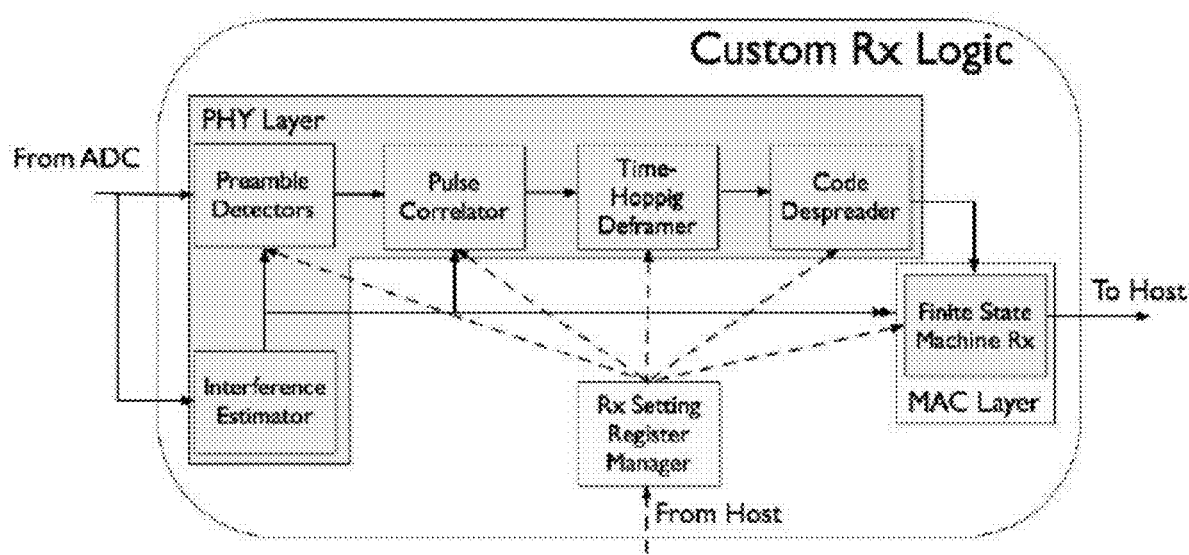
FIG. 21 is a block logic diagram of a custom receiver according to one embodiment of the present invention.

Custom Receiver Chain. The custom receiver chain, illustrated in FIG. 21, implements receiver UsWB PHY and MAC layer functionalities. The received ultrasonic signal is converted to an electrical signal by the RX transducer. The signal is amplified by the LNA, and analog-to-digital converted by the USRP ADC. Then, the digital waveform is processed by the custom receiver chain in the FPGA. After PHY and MAC operations, the custom receiver chain outputs a binary stream representing the received decoded data.

Receiver MAC Finite State Machine. The Receiver MAC Finite State Machine (FSM-RX) implements UsWB MAC protocol functionalities and coordinates the PHY-layer logic. The FSM-Rx detects the received packet based on information coming from preamble detectors, and triggers the PHY layer module to start processing the received waveform. Finally, it decodes the received bits based on the output of the PHY layer operations on the received digital waveforms. Moreover, FSMRx estimates the level of interference, and accordingly chooses the optimal pair of time-hopping frame length and spreading code length, i.e., those that maximize the communication throughput while keeping the bit error rate (BER) under a predefined threshold.

Preamble Detectors. The preamble detectors are designed to achieve packet and time-hopping synchronization. The former enables coarse synchronization by identifying the presence of an incoming packet. The latter identifies the exact start point of the time-hopping frame.

The Packet Synchronization Preamble (PSP) consists of a train of pulses positioned in consecutive time slots. The PSP detector includes a single-rate FIR filter used as a correlator, a squaring module, an integrator, and a threshold-based plateau detector. The FIR filter is used to correlate the incoming pulses with a 5th-order derivative gaussian pulse, the filter impulse response. Squaring and integrating the correlator output ideally results in a constant output for the whole PSP duration, i.e., a plateau. Therefore, the packet can be coarsely detected by finding the plateau. By using a dynamic threshold adaptation, this procedure can be made independent of the noise floor.

Fine synchronization is performed by the Time-Hopping Synchronization Preamble (THSP) detector, which includes a single-rate FIR filter used as correlator, and a threshold-based correlation peak detector. The THSP consists of a train of pulses, each positioned in the first time slot of consecutive time-hopping frames. By correlating the THSP with a $5^{th}$-order derivative gaussian pulse, a peak is obtained in the first slot of each time-hopping frame. The beginning of the timehopping frame is determined by the threshold-based peak detector. Again, the threshold is dynamically adapted to the noise floor level.

Receiver PHY Layer. The receiver PHY layer module implements the bit decoding operations that can be formally expressed as $$\sum_{j=0}^{N_s-1} a_j \int_{c_j T_c - jT_f}^{(c_j+1)T_c - jT_f} s(t) \cdot c(t) dt \genfrac{}{}{0pt}{}{>d_{-1}}{<d_1} 0, \quad (3)$$

where c(t) is the correlator function, while all the other symbols follow the signal model presented above.

The first module in the receiver PHY chain is the Pulse Correlator, i.e., a decimator FIR filter with a 5th-order derivative gaussian pulse impulse response. The Pulse Correlator outputs one sample per time slot, and the FIR impulse response, i.e., the correlator function c(t), is selected in such a way as to give a zero output for an empty slot, a positive value for a slot containing a '−1' chip, and a negative value for a slot containing a '1' chip. The correlation output goes into the Time-Hopping Deframer, which collects the non-zero inputs located according to the Time-hopping sequence used at the transmitter. The Time-Hopping Deframer determines the integral intervals and the Pulse Correlator performs the actual integration in (3). Finally, the Code Despreader inverts the spreading operation by weighting the correlation output with the spreading code originally used at the transmitter and summing these over the spreading code length. This operation corresponds to the weighted sum in (3). Based on the result of the despreading operation, the FSM-Rx makes a decision on the received bits. If the resulting sum is positive a '−1' symbol is received ($d_{-1}$), otherwise a '1' symbol is received ($d_1$).

Receiver Setting Register Manager. The Receiver Setting Register Manager (SRM-Rx) provides the same functionalities as the SRM-Tx. The SRM-Rx operates on registers different than those used in the transmission chain. Therefore, the transmitter and receiver chains of each node can be independently reconfigured in real time.

Interference Level Estimation. The Interference Level Estimation module is needed by the UsWB MAC protocol to perform the rate-maximizing adaptation. The level of interference is estimated in terms of number of interfering pulses per time-hopping frame. The estimation module consists of a single-rate FIR filter whose impulse response is a 5th-order derivative gaussian pulse, a squaring module, an integrator and a peak detector with dynamically adapted threshold. By comparing at each time slot the integrator output with the threshold, the presence of pulses can be detected, and therefore how many pulses are received in a time-hopping frame. The level of interference may be obtained by averaging over the entire packet reception time.

UsWB Prototype Performance Evaluation

The physical layer performance of the prototype is evaluated in terms of BER by varying the transmit power, the time-hopping frame and spreading code length and the level of interference in the channel. Then, MAC adaptation is shown to allow a pair of nodes to adapt the communication rate according to the level of ultrasonic interference, to maximize the throughput while satisfying packet drop rate reliability constraints.

Figure 22:
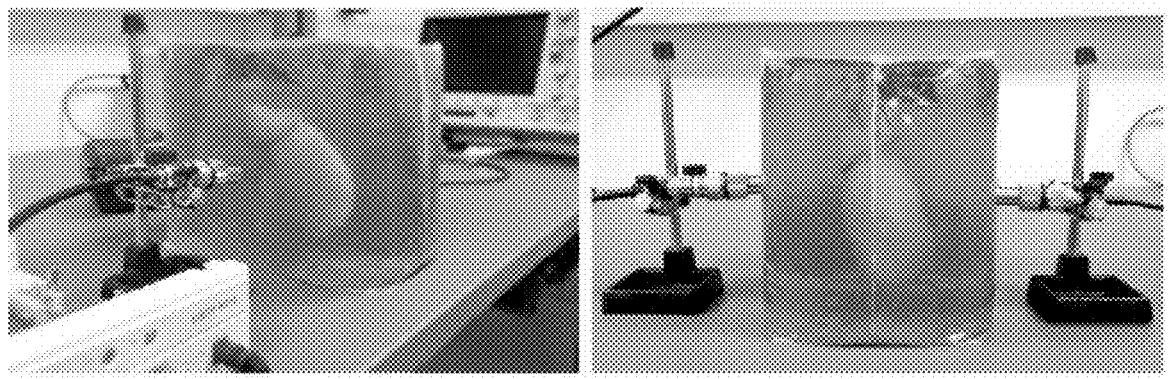
FIG. 22 is a set of images showing two nodes communicating through a human-kidney phantom according to one embodiment of the present invention.

UsWB PHY Layer. The testbed setup consists of two ultrasonic software-defined nodes communicating through a human-kidney phantom (FIG. 22). The two nodes ultrasonic transducers are positioned in the opposite sides of the phantom smaller dimension, i.e., 10 cm, and the kidney is centered in the background gel such to be aligned between the two ultrasonic transducers. To guarantee repeatability of the experiments, interference was generated from co-located transceivers artificially by injecting interfering pulses at the transmitter. The position of the interfering pulses inside the time-hopping frame is given by a pseudo-random generator HDL module, i.e., a Linear Feedback Shifter Register (LFSR).

BER Vs SNR. First, BER is evaluated as a function of the SNR per pulse measured at the receiver, in the absence of external interference, with fixed time-hopping frame and spreading code length. The SNR per pulse is defined as the ratio between the energy per pulse $E_p$ and the noise power spectral density $\eta$.

Figure 23:
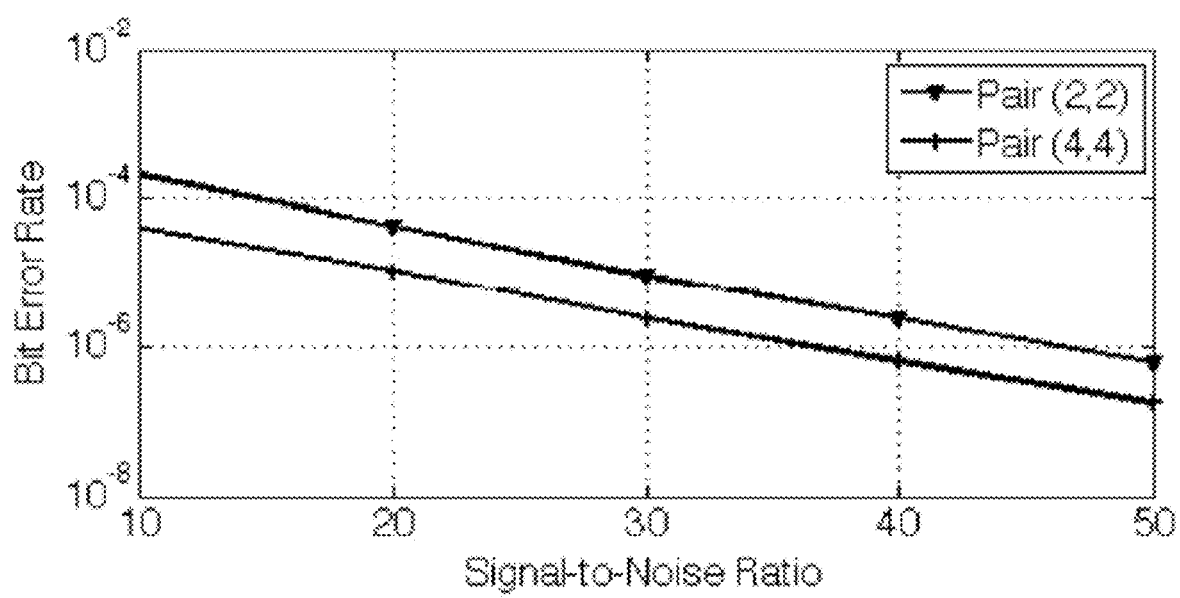
FIG. 23 is a graph showing BET in the absence of interference as a function of the SNR according to one embodiment of the present invention.

By connecting a variable-gain attenuator between the LFTX daughterboard and the power amplifier, the input power is varied at the Tx transducer between 22 dBm and −17 dBm, to obtain values of SNR between 50 to 10 dB, respectively. In FIG. 23, the resulting BER is depicted for time-hopping frame length and spreading code length pairs (2,2) and (4,4). The BER is a decreasing function of the SNR and that by using longer time-hopping frame and spreading code the BER is further reduced. If the SNR is further decreased at the receiver, i.e., to 0 dB (a transmit power of −27 dBm), communication fails altogether due to limitations in the current time synchronization scheme. In the considered "kidney" setup, the UsWB prototype achieves 173.75 kbit/s with a $10^{-6}$ BER at 40 dB SNR, which corresponds to an input power at the Tx transducer of about 13 dBm ($\approx$20 mW). A data rate up to about 700 kbit/s can be achieved (also with $10^{-6}$ BER) with a (2,2) pair increasing the input power to 22 dBm ($\approx$158 mW), i.e., 50 dB SNR. Ultra-low-power transmissions are also possible by compensating with longer time-hopping frame and spreading code. For example, in the current implementation the $T_x$ power can be reduced to −17 dBm ($\approx$19 µW), i.e., 10 dB SNR, by using a 15-slot time-hopping frame and a 20-chip spreading code, to obtain a data rate of 9 kbit/s (again with a $10^{-6}$ BER).

Energy conversion losses can be reduced with custom-designed ultrasonic transducers with higher coupling electromechanical efficiency to further reduce the Tx power requirements. Moreover, there is room for improving the current time synchronization scheme, after which it will be possible to operate at even lower SNRs.

Figure 24A:
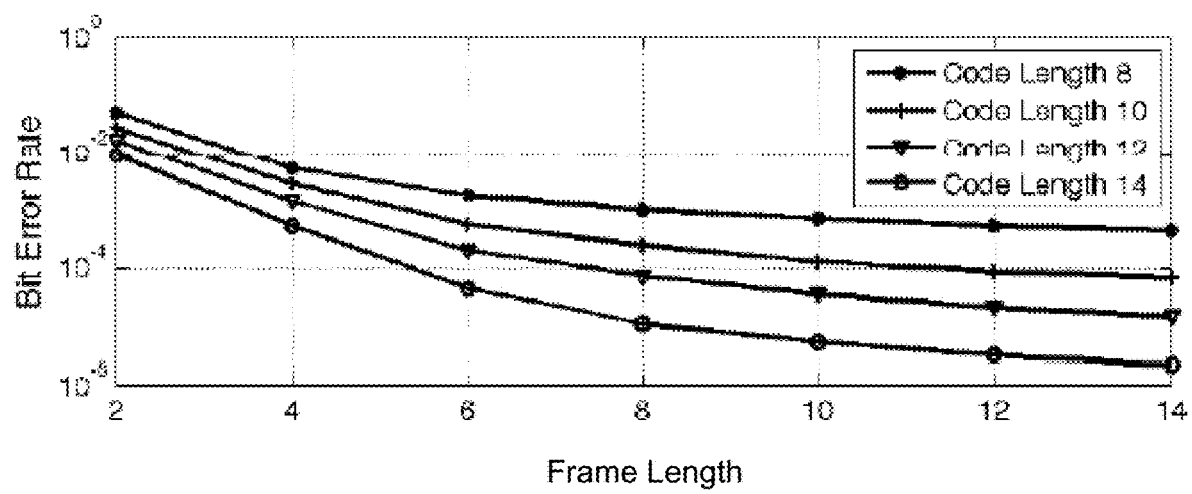
FIG. 24a is a graph showing BER as a function of frame length, with four interfering pulses per frame for different values of code length, according to one embodiment of the present invention.
Figure 24B:
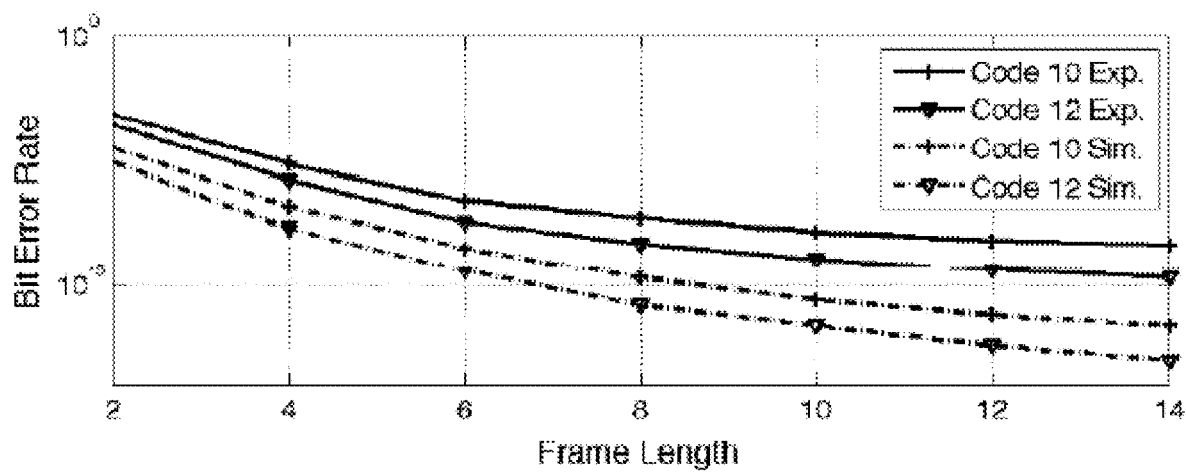
FIG. 24b is a graph showing BER as a function of frame length, with four interfering pulses per frame for different values of code length compared with simulated BER, according to one embodiment of the present invention.

BER Vs Time-Hopping and Spreading Code. The BER is evaluated by varying the time-hopping frame and spreading code length with 4 interfering pulses per frame (FIG. 24a). The input power at the Tx transducer is set to 13 dBm, i.e., 40 dB SNR. In FIG. 24b the experimental results are compared with BER curves obtained by simulating the same scenario with the UsWB PHY layer simulator. For fairness, the pulse shape used in the simulator is obtained by recording a real pulse shape as received in testbed experiments. Therefore, the signal distortion introduced by amplifiers and transducers is considered, and the scattering and reflection effects introduced by the ultrasonic phantom. However, the imported deterministic measurement does not consider the time-variability of the real testbed conditions, e.g., operating temperature, humidity, and coupling of the transducer with the phantom surface, among others. The BER is a decreasing function of the time-hopping frame length and the spreading code length, thus confirming the simulation results.

UsWB MAC Layer. A pair of ultrasonic software-defined nodes are considered and how the UsWB MAC protocol adapts the link parameters to compensate for varying levels of interference is evaluated, i.e., multiple concurrent transmissions. The level of interference is defined in terms of number of interfering pulses within a time-hopping frame. Assuming that all nodes measure the same level of interference, that is, all network nodes are close enough to be all in the same transmission range, i.e., as in the implicitly cooperative problem, the number of interfering pulses per time-hopping frame coincides with the number of co-located active Tx-Rx pairs.

Figure 25A:
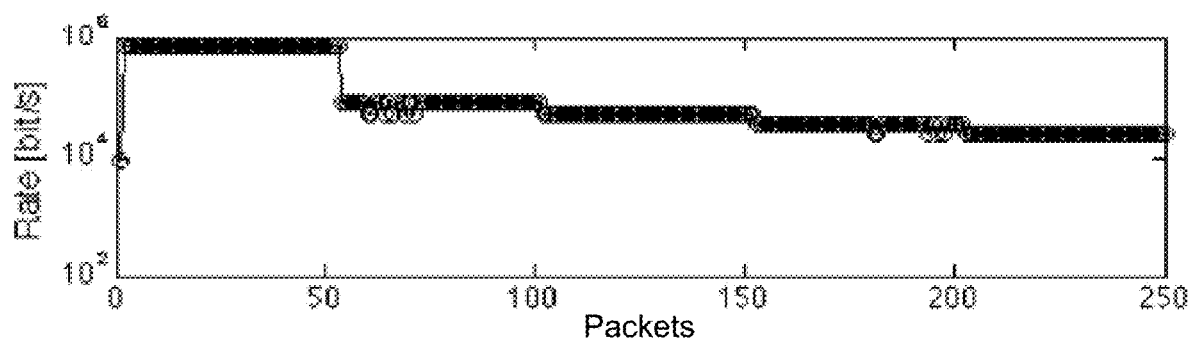
FIG. 25a is a graph showing rate-maximizing adaptation with data rate of the transmitter according to one embodiment of the present invention.
Figure 25B:
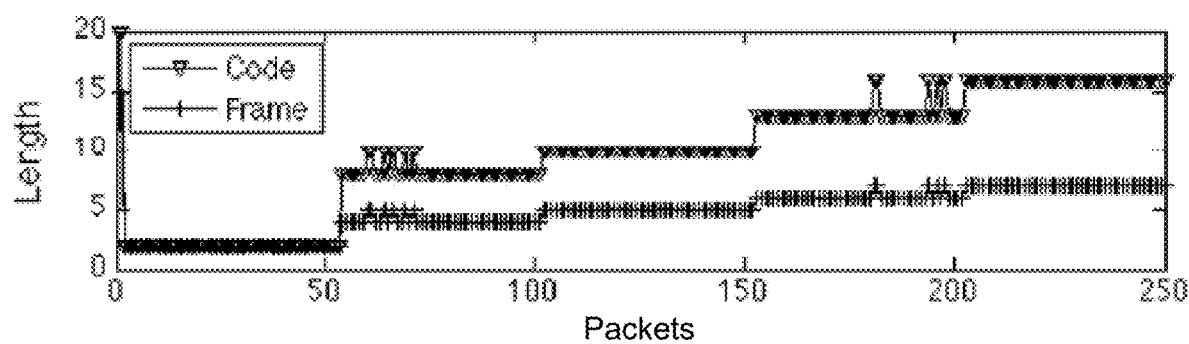
FIG. 25b is a graph showing rate-maximizing adaptation with optimal time-hopping frame and code length according to one embodiment of the present invention.
Figure 25C:
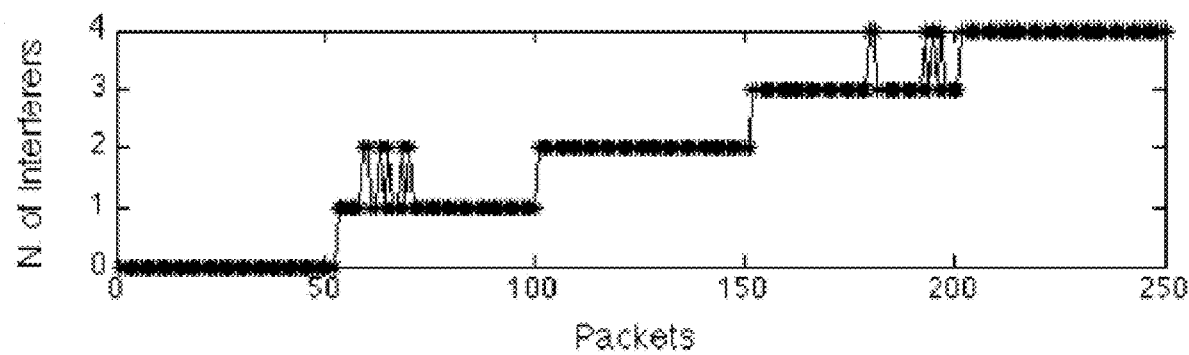
FIG. 25c is a graph showing rate-maximizing adaptation with interference estimates according to one embodiment of the present invention.

UsWB Rate-Maximizing Adaptation. First, the UsWB MAC rate-maximizing adaptation is evaluated as a function of the level of interference. 250 packets were transmitted. The level of interference is increased every 50 packets, from zero interfering pulses per time-hopping frame to four. In FIG. 25c, we show the estimated level of interference at the receiver. The receiver occasionally overestimates the number of interferers, which however does not affect the performance in terms of packet drop rate. According to the UsWB protocol, based on the interference estimation, the receiver computes the optimal pair of time-hopping frame and spreading code length, and piggybacks these in ACK/NACK packets. In the current implementation, the optimization problem is solved offline, and the solution is then loaded into the receiver. By performing a lookup table operation, the receiver finds the optimal pair corresponding to the measured level of interference and BER requirements. FIG. 25b shows the time-hopping frame and spreading code length used by the transmitter after the ACK/NACK is received. As expected, these vary according to the interference estimate at the receiver. The resulting data rate of the transmitter is shown in FIG. 25a.

Figure 26A:
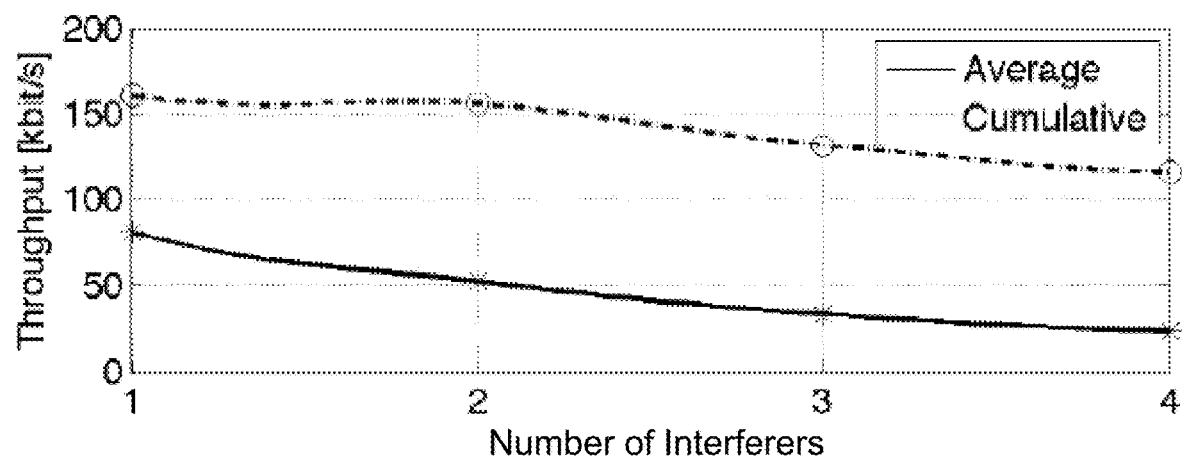
FIG. 26a is a graph showing throughput as a function of the number of interferers according to one embodiment of the present invention.
Figure 26B:
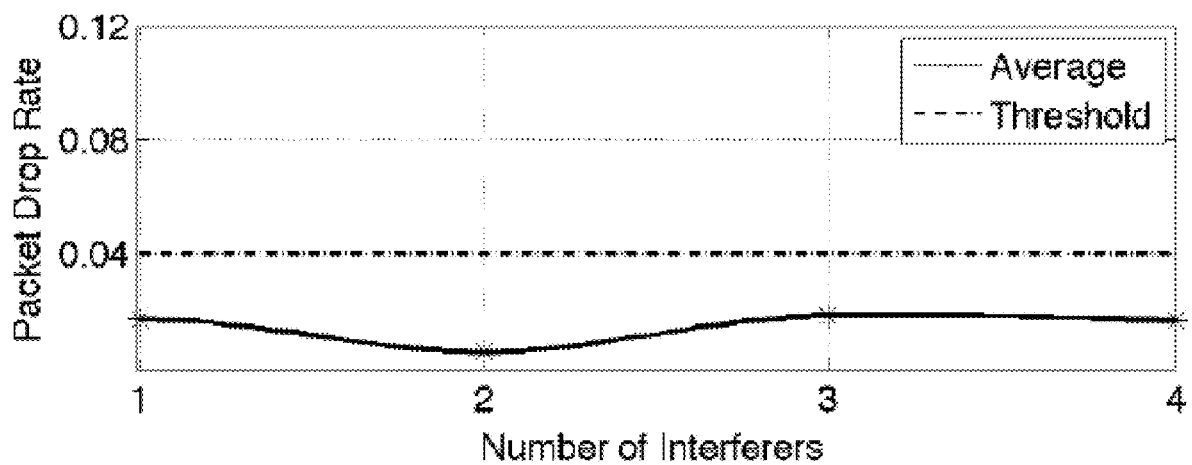
FIG. 26b is a graph showing packet drop rate as a function of the number of interferers according to one embodiment of the present invention.

Throughput and Packet Drop Rate. To verify the effectiveness of the rate adaptation, throughput and packet drop rate are evaluated at the receiver while varying the level of interference. Throughput is defined as the average bit rate of correctly received information during a time window. The packet drop rate is defined as the ratio between the number of packets dropped and the number of packets generated at the application layer. The packet payload length is set to 512 bytes and vary the level of interference from zero to four every 5000 packets. In FIG. 26a, the throughput of a single Tx-Rx pair is shown along with the cumulative throughput considering all the concurrent interfering Tx-Rx pairs. FIG. 26b shows the resulting packet drop rate compared with the maximum packet drop rate threshold (4%) corresponding to the maximum BER constraint ($<10^{-5}$) and packet size.

Figure 27A:
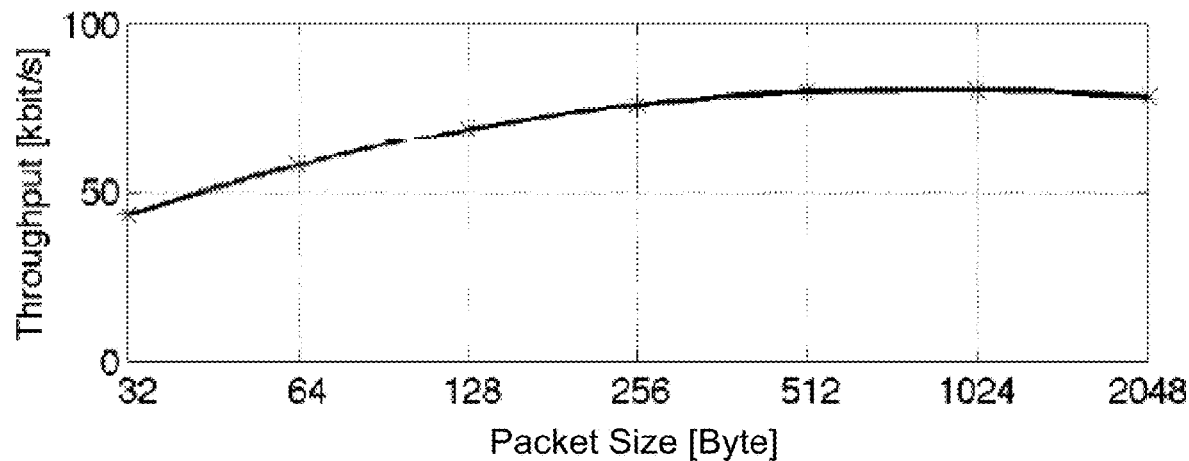
FIG. 27a is a graph showing throughput as a function of packet size with one co-located interfering Tx-Rx pair according to one embodiment of the present invention.
Figure 27B:
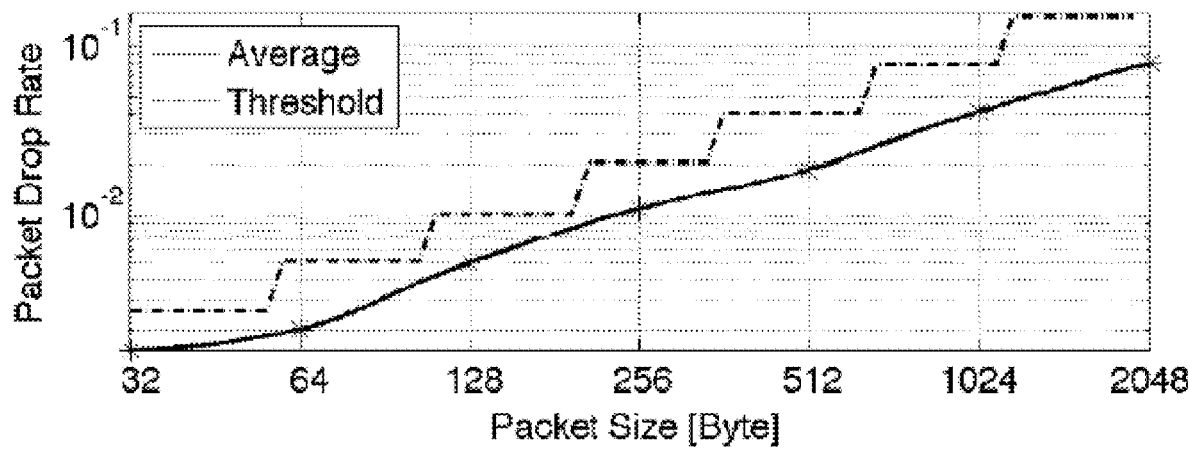
FIG. 27b is a graph showing packet drop rate as a function of packet size with one co-located interfering Tx-Rx pair according to one embodiment of the present invention.

Optimal Packet Size. Finally, how the packet size affects throughput and packet drop rate is investigated. The number of interferers is set to one, and to transmit a fixed amount of data ($\approx$2 MBytes) with different packet sizes. In FIG. 27a, we observe that the resulting throughput is maximized between 512 and 1024 bytes. The optimal packet size is influenced by the packet drop rate and protocol overhead. For a given BER, the packet drop rate is determined by the packet size, i.e., the longer the packet the higher the packet drop rate. At the same time, longer packets result in less protocol overhead (packet header, ACK/NACK control packets, and propagation delay). FIG. 27b shows that the packet drop rate increases when the payload size increases. However, the maximum packet drop rate constraint is always satisfied.

Prototype Ultrasonic Channel Characterization

The ultrasonic channel can be statistically characterized through time domain measurements. A digital sampling oscilloscope was used to record the response to a probing signal, and obtain a statistical model of small-scale fading for the ultrasonic intra-body channel.

Small-scale Fading Model. Small-scale fading describes variations of the channel over a period of time where the channel can be considered wide-sense stationary. In RF wireless communications, the signal envelope affected by small-scale fading has been typically modeled using different distributions, such as Rice, Rayleigh, Nakagami, Log-normal, and Weibull To this purpose, short ultrasonic pulses are transmitted through the ultrasonic phantom. The output is recorded by connecting an Rx transducer to a digital sampling oscilloscope, and process the collected data to identify the statistical distribution that best fits the recorded envelope distribution.

Figure 28:
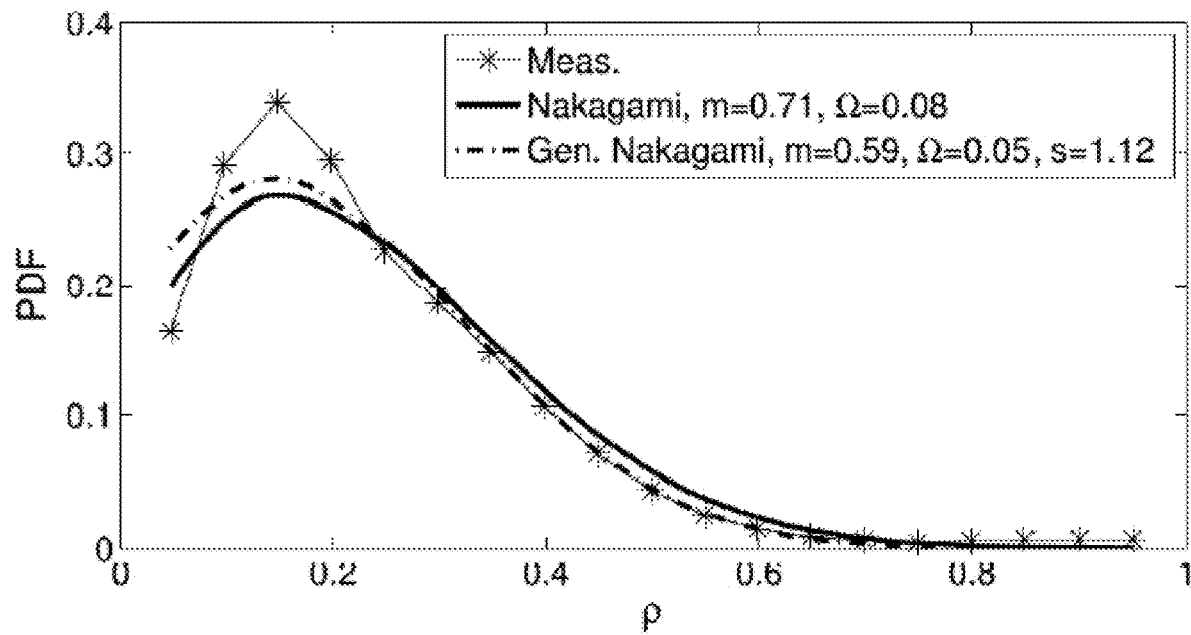
FIG. 28 is a graph showing recorded envelope distribution least-square fitted with Nakagami and generalized Nakagami distributions according to one embodiment of the present invention.

In FIG. 28 the recorded envelope distribution is shown. The experimental result is least-square fitted with a Nakagami and a generalized Nakagami distribution. The probability density function (PDF) of the signal envelope p can be expressed as $$f(\rho; m, \Omega, s) = \frac{2sm^m \rho^{2sm-1}}{\Gamma(m)\Omega^m} e^{-\frac{m}{\Omega}\rho^{2s}} U(\rho), \quad (4)$$

where m is the Nakagami parameter, $\Omega$ is a scaling parameter, s is the generalization parameter, $U(\cdot)$ is the unit-step function, and $\Gamma(\cdot)$ is the gamma function. For s=1, (4) gives the original Nakagami distribution. Nakagami distributions allow to match empirical data in very general environments, under various scattering conditions. By varying the value of the Nakagami parameter m, different distributions are obtained such as Gaussian distribution (m=0.5), generalized Rice distribution (0.5<m<1), Rayleigh distribution (m=1) and Rice distribution (m>1). Parameters takes into account the so-called tail effect. When s<1, the distribution presents heavy upper tails; for s>1, there are shorter upper tails. Therefore, the Nakagami amplitude distribution can describe different scenarios by simply varying the value of m and s.

In both cases, the matched values of m correspond to a generalized Rice distribution, which is typically encountered in the presence of randomly located scatterers together with periodic alignment of scatterers. This is indeed the case for the human-kidney phantom used in the experiment, which consists of a scattering medium, and whose boundary may represent potential aligned scatterers. Similar results have been observed in medical ultrasonic imaging. For example, the amplitude statistics of a signal reflected from a human-kidney were modeled using a Nakagami distribution.

Exemplary Embodiment

Figure 29:
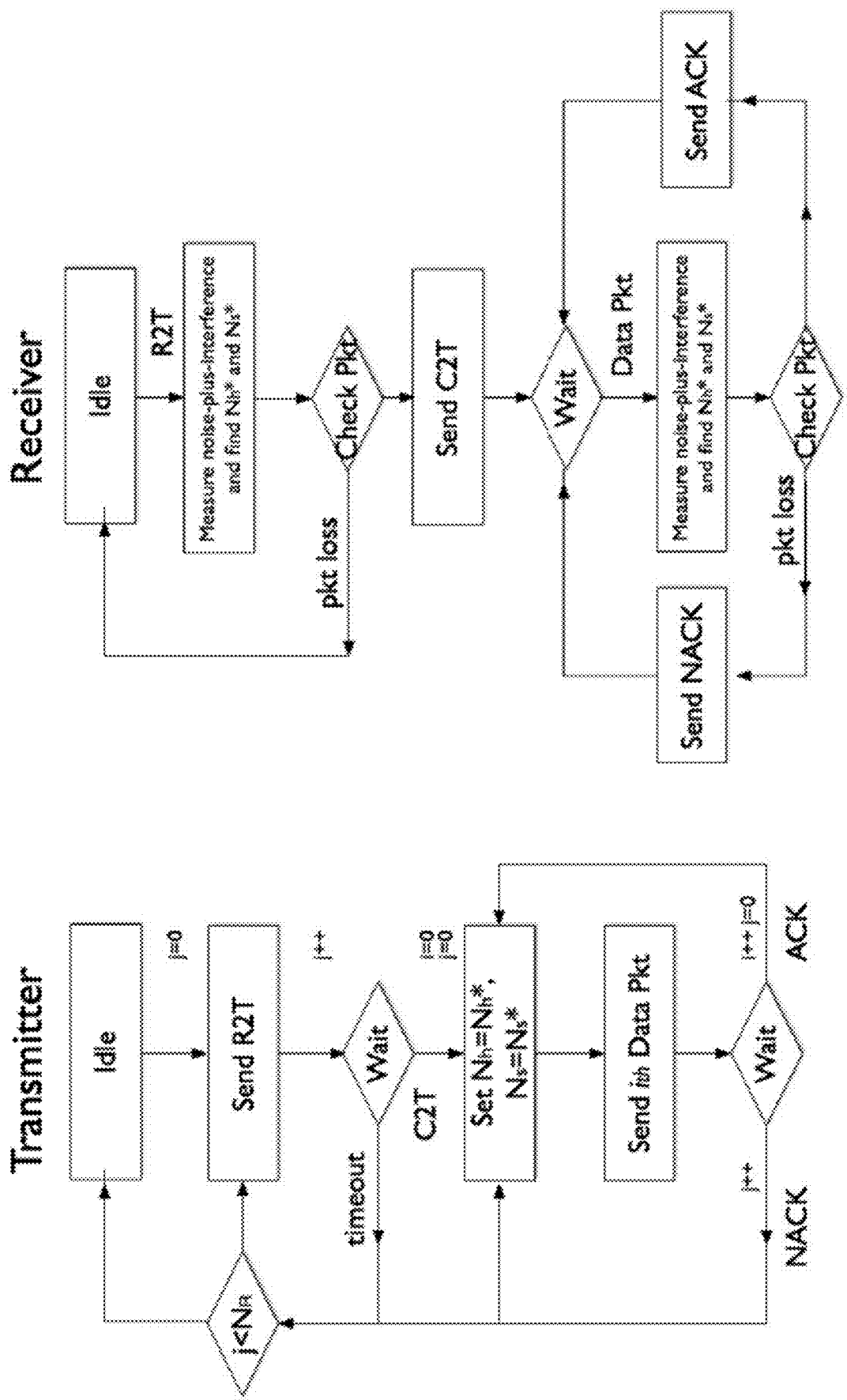
FIG. 29 is a block diagram showing one embodied method of the present invention.

FIG. 29 provides a detailed schematic of one embodiment of the present invention. The following abbreviations are used in this exemplary embodiment:

Given for each transmitter-receiver pair r in $\mathcal{N}$, the set of $|\mathcal{N}|$ existing connections:
  $P_r$: The average power per pulse period emitted by the transmitter in the $r^{th}$ connection
  $g_{r,r}$: The path gain between the transmitter and receiver in the $r^{th}$ connection
  $g_{i,r}$: The path gain between the $i^{th}$ interferer and the receiver in the $r^{th}$ connection
  $I_r$: The set of the connections interfering with the $r^{th}$ connection
  $P_i$: The average power per pulse period emitted by the $i^{th}$ interferer in $I_r$
  $N_{i,h}$: The time-hopping frame length used by the $i^{th}$ interferer in $I_r$
  $T_c$: Time duration of a time slot
  $\sigma$: An adimensional parameter depending on the shape of the transmitted pulse and the receiver correlator
  $\eta$: The background noise energy $$SINR_r = N_{s,r} \frac{P_r g_{r,r} N_{h,r} T_c}{\eta + \sigma^2 \sum_{i \in I_r} \frac{N_{h,r}}{N_{h,i}} P_i g_{i,r}};$$

The signal to interference-plus-noise ratio of at the receiver in the $r^{th}$ connection
  $R_{min}$: The minimum data rate required
  $SINR_{min}$: The minimum SINR required
  $E_p$: The energy required per pulse transmission
For each transmitter-receiver pair in $\mathcal{N}$, find:
  $N_{h,r}$: The time-hopping frame length used by the $r^{th}$ transmitter
  $N_{s,r}$: The spreading code length used by the $r^{th}$ transmitter
that:
maximize the data rate $$R = \frac{1}{N_h N_s T_c},$$

or minimize the energy per bit, $E_b = E_p N_s$, or minimize the average energy emitter per second, $$E_s = \frac{E_p}{T_c N_h}$$

subject to: $R > R_{min}$, $SINR_r > SINR_{min}$

No order should be given to the steps of the following embodiment of the present invention.

Step 1: When TX needs to transmit a packet, it first needs to reserve a dedicated channel to RX. The connection is opened through the common control channel, which is implemented through a unique time-hopping sequence and a spreading code known and shared by all network devices. In the two-way handshake procedure, TX sends a Request-to-Transmit (R2T) packet to RX, which contains its own ID. During step 1, since an estimate of the current interference level is not available, the transmitter sets $N_h$ and $N_s$ to the maximum value supported, $N_{h,max}$ and $N_{s,max}$. Therefore RX transmits conservatively at the minimum data rate at rate $$R = \frac{1}{N_{h,max} N_{s,max} T_c}.$$

in the meanwhile, the receiver measures the power of noise-plus-interference.

Step 2: If RX is idle, it receives the R2T, and in the meanwhile measures the level of power of the noise-plus-interference in the channel. If the R2T is correctly decoded, RX sends back to TX a Clear-to-Transmit (C2T) control packet. If RX is busy, R2T will not be received, and, thus, C2T will not be sent. If R2T is not correctly decoded, i.e., a loss, C2T will not be sent. If C2T is not sent prior to timer expiration at the transmitter, TX will attempt a new transmission after a random backoff time, for a maximum of NR times.

The receiver RX, based on the level of power of the noise-plus-interference measured in the channel, computes the optimal time-hopping frame length and spreading code lengths, $N_h^*$ and $N_s^*$, and embeds this information in the C2T packet. After a C2T is sent, the receiver switches to a dedicated channel by computing a private time-hopping sequence and spreading code obtained by seeding a pseudo-random sequence generator with the transmitter ID.

Step 3: After receiving the C2T, the transmitter switches to a dedicated channel by computing the same private time-hopping sequence and spreading code computed by the receiver by seeding a pseudo-random sequence generator with its own ID. Once the connection has been established, TX sends the first data packet using the optimal time-hopping frame length and spreading code length calculated by the receiver, $N_h = N_h^*$ and $N_s = N_s^*$, and therefore the transmission data rate $$R = \frac{1}{N_h^* N_s^* T_c}.$$

Go to step 2. At this step both TX and RX have already left the common channel and switched to a dedicated channel. In the explicitly cooperative case once the communication has been established, RX does not leave the common control channel. Instead, it keeps "listening" to both the dedicated and common control channel at the same time. In the dedicated control channel, as in step 4, RX sends to TX the optimal frame and code lengths to be used for the next transmission. In the common control channel, when a variation in the measured level of interference is registered, RX exchanges with other co-located receivers information on the level of tolerable interference.

Step 4: For each received data packet, the receiver RX checks if it has been correctly decoded, and based on the level of interference measured in the channel, computes the optimal time-hopping frame and spreading code lengths, $N_h^*$ and $N_s^*$. This information is piggybacked into an Acknowledgment (ACK) packet, in case of correct packet decoding, or Negative-Acknowledgment (NACK) packet, in case of an incorrect packet decoding, i.e., a loss.

Step 5: For each data packet to transmit, the transmitter updates the transmission time-hopping frame length $N_h = N_h^*$ and spreading code length $N_s = N_s^*$ and therefore the transmission data rate $$R = \frac{1}{N_h^* N_s^* T_c}.$$

Go to Step 4.

Figure 30:
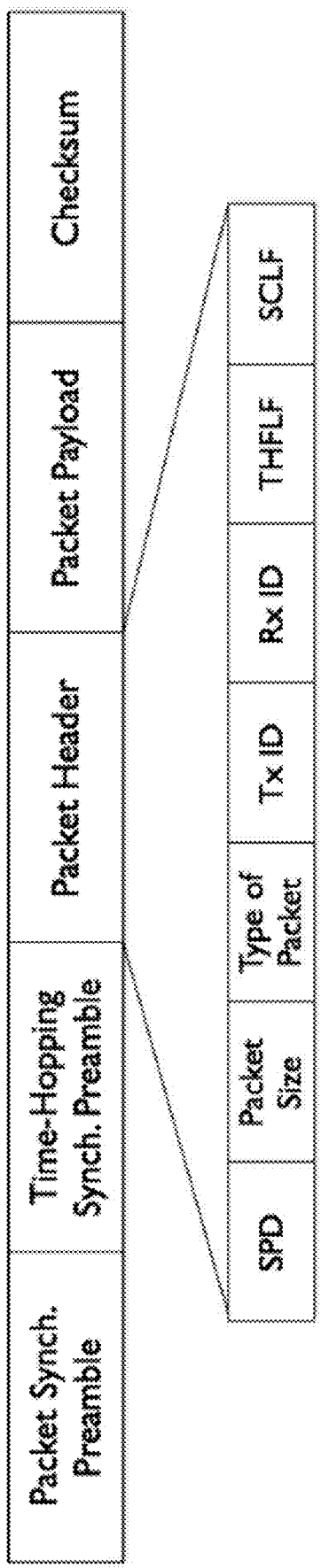
FIG. 30 is a diagram showing a UsWB packet structure according to one embodiment of the present invention.

FIG. 30 illustrates the components of the data packet. The UsWB packet starts after a Packet Synchronization Preamble (PSP) and a Time-Hopping Synchronization Preamble (THSP). The former enables coarse synchronization that allows the receiver to detect an incoming packet, while the latter allows identifying the exact start time of the time-hopping frame. A 16-bit Start Packet Delimiter (SPD) delimits the packet header. This is followed by a 16-bit MAC Packet Size field representing the payload length in bytes. Then, a 3-bit Type of Packet is used to distinguish between R2T and C2T packets, ACK and NACK packets, and data packets. This is followed by two 6-bit fields representing the transmitter and receiver ID. Finally, an 8-bit Time-Hopping Frame Length Feedback (THFLF) and an 8-bit Spreading Code Length Feedback (SCLF) contain the feedback values piggybacked in ACK or NACK packets. The payload has a variable length, from 0 to 32767 byte. R2T and C2T packets have no payload. ACK and NACK packets have a payload if piggybacked. Finally, a 16-bit packet checksum follows the payload to verify that the packet has been received correctly. The checksum calculation includes the all packet structure, i.e., both the header and the payload.

Each sensor node operates via an embedded computing unit. The process can also be adapted to operate with a central node.

The BAN or BSN may monitor and, optionally, regulate, blood pressure, blood oxygen level, respiratory rate, carbon dioxide level, oxygen saturation, heart rate, cardiac output, blood pressure, pulmonary pressure, body temperature, fluid level, brain function, intracranial pressure, blood sugar, etc.

The actuator may be a medicine pump, cardiac regulator, oxygen tank regulator, or other bodily function regulator. In one embodiment, the medicine pump is an insulin pump.

The following are exemplary ranges and examples of UsWB parameters:
  Frequency range: from 500 kHz to several GHz (around 5 MHz in the simulation and the implementation)
  Spreading code: pseudo-random pseudo-orthogonal codes
  Spreading code length: from 1 to 2048
  From 2 to 20 in the simulation and the implementation
  Time-hopping sequence: pseudo-random sequence
  Time-hopping frame length: from 1 to 2048 (From 2 to 15 in the simulation)
  Payload size: from 0 to 32767 byte
  Preamble lengths: from 1 pulse to 4096
  Time-slot duration and pulse duration from 10 microseconds down to few picoseconds (Pulse duration: around 420 ns in the simulation and around 300 ns in the implementation, Time-slot duration: around 500 ns in the simulation and around 360 ns in the implementation)
Number of chips per frame: 1 per each transmission in each node.

In FIG. 13, each plot in the figure represents the time evolution of code length (top) and frame length (bottom) for each user. In the implicit cooperative problem all the nodes adapt to the same optimal pair, thus the plots overlap, except for the opening connection time instants (approximately every 5 seconds apart), where the maximum allowed code and frame lengths are used. Therefore, the markers in the plot represent a different node joining the Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method for receiving transmitted data through biological tissue using ultrasonic pulses comprising:
  receiving, at a receiver, a request-to-transmit packet from a transmitter, the packet containing a ID of the transmitter;
  measuring, at the receiver, an interference value;
  sending, from the receiver, a clear-to-transmit packet to the transmitter comprising feedback data based on the interference value;
  calculating a pseudorandom private time-hopping sequence and a pseudorandom private spreading code;

establishing a connection with the transmitter using the private time-hopping sequence and private spreading code;

receiving, at the receiver, a data packet from the transmitter using the private time-hopping sequence, the private spreading code;

measuring, at the receiver, an updated interference value; and sending, from the receiver, an acknowledgement packet in response to the received data packet, the acknowledgement packet comprising updated feedback data based on the updated interference value.

2. The method of claim 1, further comprising:

calculating a forward time-hopping frame length and a forward spreading code length based on the measured interference value; and calculating an updated time-hopping frame length and spreading code length based on the updated interference value;

wherein the data packet uses the forward time-hopping frame length and the forward spreading code length;

wherein the clear-to-transmit packet comprises the calculated forward time-hopping frame length and the forward spreading code length; and wherein the acknowledgement packet comprises the updated time-hopping frame length and the updated spreading code length.

3. The method of claim 1, further comprising the step of decoding the request-to-transmit packet.

4. The method of claim 1, wherein the clear-to-transmit packet is transmitted at a predetermined time-hopping frame length and a predetermined spreading code length.

5. The method of claim 1, wherein each packet contains a synchronization preamble.

6. The method of claim 5, further comprising correlating the received packet with the synchronization preamble to identify a starting point of the packet.

7. The method of claim 1, wherein the synchronization preamble comprises a pseudo-random noise sequence of variable length or a chirp sequence of variable length.

8. The method of claim 1, wherein the interference value is the summation of measured interference and noise.

* * * * *